United States Patent
Koglin et al.

(10) Patent No.: US 11,959,117 B2
(45) Date of Patent: Apr. 16, 2024

(54) METHODS AND COMPOSITIONS FOR THE ENZYMATIC PRODUCTION OF PSEUDOURIDINE TRIPHOSPHATE

(71) Applicant: Natures's Toolbox, Inc., Rio Rancho, NM (US)

(72) Inventors: Alexander Koglin, Santa Fe, NM (US); Michael Humbert, Santa Fe, NM (US); Matthias Strieker, Santa Fe, NM (US); Grant Eliason, Rio Rancho, NM (US)

(73) Assignee: NATURE'S TOOLBOX, INC., Rio Rancho, NM (US)

( * ) Notice: Subject to any disclaimer, the term of this patent is extended or adjusted under 35 U.S.C. 154(b) by 0 days.

(21) Appl. No.: 18/206,319

(22) Filed: Jun. 6, 2023

(65) Prior Publication Data
US 2023/0383328 A1 Nov. 30, 2023

Related U.S. Application Data

(63) Continuation-in-part of application No. PCT/US2023/064934, filed on Mar. 24, 2023.

(60) Provisional application No. 63/323,145, filed on Mar. 24, 2022.

(51) Int. Cl.
C12P 19/32 (2006.01)
C12N 9/12 (2006.01)
C12N 9/88 (2006.01)

(52) U.S. Cl.
CPC ............ *C12P 19/32* (2013.01); *C12N 9/1205* (2013.01); *C12N 9/1229* (2013.01); *C12N 9/88* (2013.01); *C12Y 207/01015* (2013.01); *C12Y 207/04001* (2013.01); *C12Y 402/0107* (2013.01)

(58) Field of Classification Search
CPC ........ C12P 19/32; C12P 19/38; C12N 9/1205; C12N 9/1229; C12N 9/88; C12Y 207/01015; C12Y 207/04001; C12Y 402/0107
See application file for complete search history.

(56) References Cited

U.S. PATENT DOCUMENTS 8,691,966 B2   4/2014   Kariko et al.
10,898,574 B2  1/2021   de Fougerolles et al.

OTHER PUBLICATIONS

Whisstock et al. Quaterly Reviews of Biophysics, 2003, "Prediction of protein function from protein sequence and structure", 36(3):307-340. (Year: 2003).*

Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*

Kisselev L., Polypeptide release factors in prokaryotes and eukaryotes: same function, different structure. Structure, 2002, vol. 10: 8-9. (Year: 2002).*

* cited by examiner

*Primary Examiner* — Iqbal H Chowdhury
(74) *Attorney, Agent, or Firm* — Berg Hill Greenleaf Ruscitti LLP

(57) ABSTRACT

The present invention includes novel systems, methods, and compositions for the enzymatic/chemical production of pseudouridine (Ψ) and its variants, such as N1-methyl-pseudouridine-5'-triphosphate (m1ΨTP).

22 Claims, 15 Drawing Sheets

Specification includes a Sequence Listing.

|          | mmoles | amount |
|----------|--------|--------|
| uracil   | 550    | 61.6 g added in 100 mmol batches |
| ribose   | 500    | 75 g |
| ATP      | 5      | 2.755 g |
| polyP    | 270    | 165 g |
| RbsK-DG  |        | 83.5 mg |
| PsuG-DG  |        | 90 mg |
| PPK2-DG  |        | 85.5 mg |

METHODS AND COMPOSITIONS FOR THE ENZYMATIC PRODUCTION OF PSEUDOURIDINE TRIPHOSPHATE

CROSS-REFERENCE TO RELATED APPLICATIONS

This International PCT application claims the benefit of and priority to U.S. Provisional Application No. 63/323,145, filed Mar. 24, 2022. The entire specification, claims, and figures of the above-referenced application is hereby incorporated, in its entirety by reference.

SEQUENCE LISTING

The instant application contains contents of the electronic sequence listing (90125-00252-Sequence-Listing; Size: 27,706 bytes; and Date of Creation: Aug. 17, 2023) is herein incorporated by reference in its entirety.

TECHNICAL FIELD

The present invention relates to the fields of chemical and enzymatic production of nucleotide isomers, and in particular the enzymatic and chemical production of uridine to pseudouridine (Ψ), and specifically the and chemical and/or enzymatic production and modification of N1-methyl-pseudouridine.

BACKGROUND

Pseudouridine-5'-triphosphate (ΨTP) is a C5-glycosidic isomer of uridine that contains a C—C bond between the C1 of the ribose sugar and the C5 of uracil, rather than the usual C1-N1 bond found in uridine. Pseudouridine is found in almost all types of non-coding RNA such as tRNA, rRNA, small nuclear RNA (snRNA) as well as coding RNA, all of which are generally referred to herein as "RNA," or an "RNA oligonucleotide" meaning an oligonucleotide in which several RNA nucleosides are linked. This base modification is able to stabilize RNA and improve base-stacking by forming additional hydrogen bonds with water through its extra amino group.

The most common modification to therapeutic RNAs is the partial substitution UTP with ΨTP to stabilize the RNA in the translating host cell. Pseudo-UTP is naturally occurring, for example in tRNAs, for this reason and is produced naturally by enzymes in diverse organisms called Pseudo-Uridine Synthases (pUS). These enzymes are responsible for the most abundant post-transcriptional modification of cellular RNA and catalyze the site-specific isomerization of uridine residues that are already part of an RNA oligonucleotide. Therapeutic RNAs require ΨTP as a replacement for uridine-5'-triphosphate (UTP), however the cost for synthetically produced ΨTP is prohibitively high creating a production bottle-neck for many RNA-based therapeutics, such as RNA-vaccines, and other RNA therapeutics and diagnostics that are increasingly produce by in vitro transcription systems. As such, there exists a need for an efficient and cost-effective method of producing ΨTP that can, in particular, be applied to in vitro RNA production systems.

SUMMARY OF THE INVENTION

In one aspect, the invention includes systems. methods and compositions for the production of pseudouridine. In one embodiment, the invention can include systems and methods for enzymatically synthesizing pseudouridine-5'-monophosphate (ΨMP). In this embodiment, the system can include a substrate comprising a quantity of isolated uracil nucleobase, and a quantity of isolated ribose-5-phosphate. The substrate can be introduced to a quantity of pseudouridine-5'-phosphate glycosidase (PsuG) enzyme, or a fragment or variant thereof, wherein said PsuG catalyzes the formation of pseudouridine-5'-monophosphate (ΨMP) from the uracil nucleobase with a ribose-5-phosphate.

In another aspect, the invention can further include a protecting agent that reacts with the hydroxyl groups of the ΨMP forming a protected ΨMP. The protecting agent of the invention can include an N-silyl compound, such as preferably hexamethyldisilazane (HMDS), wherein the HMDS reacts with the ΨMP forming a protected ΨMP compound as described herein.

In another aspect, the invention can further include a methylating agent that reacts with the protected ΨMP, forming a protected pseudouridine-5'-monophosphate (protected m1ΨMP) compound. In a preferred aspect, the methylating agent of the invention comprises iodomethane.

In another aspect, the invention can further include a deprotection agent that reacts with the protected m1ΨMP to remove the protecting group(s) thereby forming N1-methyl-pseudouridine-5'-monophosphate (m1ΨMP). In a preferred aspect, the deprotection agent of the invention includes a quantity of ammonia and methanol.

In another aspect, the invention can further include a phosphorylating agent that catalyzes the sequential phosphorylation of m1ΨMP forming N1-methyl-pseudouridine-5'-diphosphate (m1ΨDP), and N1-methyl-pseudouridine-5'-triphosphate (m1ΨTP). In a preferred aspect, the phosphorylating agent of the invention includes a quantity of Polyphosphate kinase (PPK2), or a fragment or variant thereof, and a quantity of inorganic polyphosphate, wherein said PPK2, or fragment of variant thereof, catalyzes the sequential phosphorylation of m1ΨMP to form m1ΨDP and m1ΨTP. In a preferred aspect, the PPK comprises a PPK from a thermophilic bacteria, such as for example from the genus *Deinococcus* or *Meiothermus*, or more preferably from thermophilic bacteria including *Deinococcus geothermalis, Deinococcus radiodurans,* or *Meiothermus ruber.* In still further preferred aspects, the PPK of the invention includes a sequence according to SEQ ID NO. 4, 6, 21, or a sequence having at least 80% homology with SEQ ID NO. 4, 6, or 21.

In a further aspect of the invention, the concentration of inorganic polyphosphate is in excess, such that it promotes the forward reaction of the sequential phosphorylation of m1ΨMP to form m1ΨDP and m1ΨTP. Moreover, in this preferred aspect, the sequential phosphorylation of m1ΨMP by PPK is performed at a temperature, and preferably in the presence of excess inorganic polyphosphate generating reaction conditions that causes the forward reaction of the sequential phosphorylation of m1ΨMP to form m1ΨDP and m1ΨTP.

In another aspect, the PsuG of the invention can include a PsuG from a an enteric bacteria, or a thermophilic bacteria, such as *Deinococcus geothermalis,* and/or *Escherichia coli* respectively. In still further preferred aspects, the PsuG of the invention can include a sequence selected from SEQ ID NO. 1, 3, or a sequence having at least 80% homology with SEQ ID NO. 1 or 3. In another preferred embodiment, the concentration of the uracil nucleobase and ribose-5-phosphate substrates and reaction temperature cause the reverse catalyzation of the substrates by the PsuG forming the ΨMP.

In another aspect, the invention includes systems, methods, and compositions for the production of ribose-5-phosphate. In this preferred embodiment, a quantity of isolated Ribokinase (RbsK) enzyme, or a fragment or variant thereof, and a quantity of ribose such that the RbsK catalyzes the formation of said ribose-5-phosphate from said ribose in the presence of an adenosine-triphosphate (ATP) donor, which donates a phosphate group to the ribose to form the ribose-5-phosphate and an adenosine-diphosphate (ADP). In another aspect, the RbsK if the invention can include an RbsK from a thermophilic bacteria, such as *Deinococcus geothermalis*. In another aspect, the RbsK if the invention can include a sequence according to SEQ ID NO. 20, or a sequence having at least 80% homology with SEQ ID NO. 20.

Additional embodiments of the invention include and isolated compound selected from: ΨMP, protected ΨMP, protected m1ΨMP compound, m1ΨMP, m1ΨDP, and m1ΨTP produced by the methods, systems and composition of the invention.

In another aspect the present invention includes novel systems, methods, and compositions for the enzymatic production of pseudouridine (Ψ). In a preferred aspect, Ψ, and preferably pseudouridine-5'-triphosphate (ΨTP) may be enzymatically produced from raw RNA samples, preferably extracted from the fermentation or cellular waste of bacterial cultures routinely grown in laboratories or yeast waste product from the beer and wine fermentation industry. In this aspect, RNA is isolated from the fermentation waste and enzymatically converted into a Ψ form, which is further enzymatically converted into its mono-phosphate form (ΨMP) prior to tri-phosphate regeneration. In one preferred aspect, tri-phosphate regeneration is accomplished using inorganic polyphosphates (PPi) and adenosine mono-phosphate (AMP) as part of a dual enzyme system, which may preferably include adenosine kinase (AdK) and polyphosphate kinase (PPK) to regenerate ΨTP from ΨMP.

In a preferred aspect of the invention, N1-methyl-pseudouridine tri-phosphate (m1Ψ) may be generated from isolated uridine continuing RNA oligonucleotides. In this preferred aspect, RNA containing uridine may be isolated from, for example, fermentation waste. The uridine residues of the RNA oligonucleotide may be converted to pseudouridine-5'-triphosphate (Ψ) by pseudouridine synthase (pUS). Next, the Ψ residues may be methylated forming m1Ψ residues by N1-pseudouridine methyltransferase which can be further digested into nucleotide mono-phosphates (m1ΨMP), preferably by a nuclease, such as P1 or a 5'-Phosphodiesterase (5'-PDase). The resulting m1ΨMP can be purified and enzymatically converted into m1Ψ tri-phosphate by a nucleoside diphosphate kinase (NdK), such as adenosyl kinase in the presence of an adenosine-triphosphate (ATP) donor.

In another preferred embodiment, the invention includes a modified N1-pseudouridine methyltransferase, or a fragment or variant thereof, that may further catalyze the methylation of the newly formed Ψ residues in a RNA oligonucleotide forming a series of N1-methyl-pseudouridine (m1Ψ) residues. In one preferred embodiment, the 129R and 132R resides of an exemplary N1-pseudouridine methyltransferase Nep1 are converted to 129A and 132A forming a modified N1-pseudouridine methyltransferase (mNep1). These engineered mutations may allow the formation of individual N1-methyl-pseudouridine (m1Ψ) residues from the Ψ residues of the RNA oligonucleotide by reducing the coordination of mNep1 with the nucleotide adjacent to the pUTP residues in the RNA oligonucleotides.

In another aspect, the present invention includes alternative novel systems, methods, and compositions for the enzymatic production of ΨTP utilizing a pseudouridine-5'-phosphate glycosidase (PsuG) enzyme. In this preferred aspect, PsuG may be used to catalyze the formation of pseudouridine-5'-monophosphate (ΨMP) from a uracil nucleobase with a ribose-5-phosphate substrate. The temperature and substrate concentrations of this reaction cause the reverse action of the PsuG enzyme which, under normal conditions, catalytically cleaves a ΨMP substrate to form uracil and ribose-5-phosphate. The resulting ΨMP can be enzymatically converted into Ψ tri-phosphate by a nucleoside diphosphate kinase (NdK), such as adenosyl kinase (Adk) in the presence of an adenosine-triphosphate (ATP) donor. Alternatively, the resulting ΨMP can be enzymatically converted into Ψ tri-phosphate (ΨTP) by a deoxynucleoside kinase, such as PPK2, in the presence of a phosphate donor, which may preferably include sodium hexamethaphosphate. The ΨTP may further be optionally methylated forming m1ΨTP.

Additional aspects of the invention may be evidenced from the specification, claims and figures provided below.

DETAILED DESCRIPTION OF THE INVENTION

Figure 1:
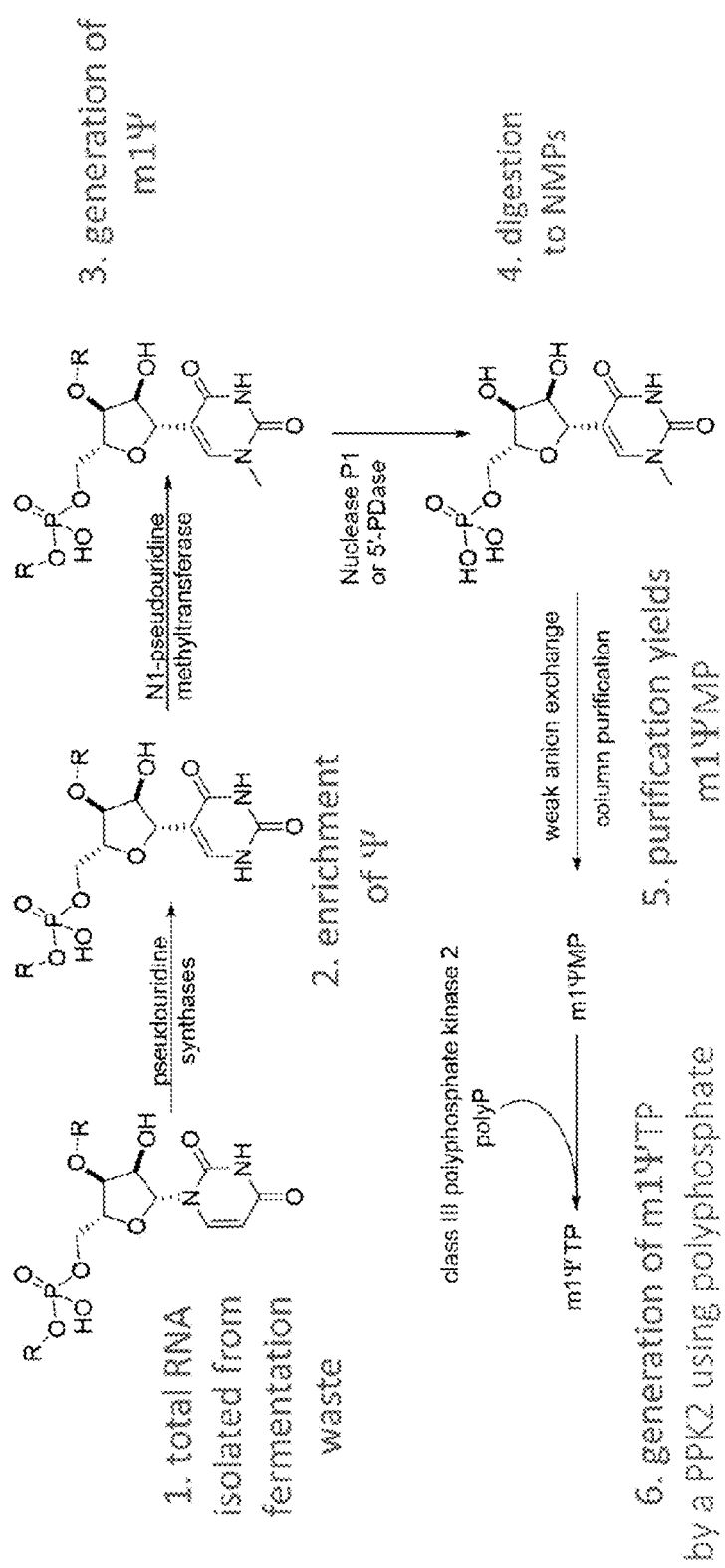
FIG. 1. shows a schematic scheme for the enzymatic production of ΨTP, and in particular m1-pseudouridine-5'-triphosphate (m1ΨTP) in one embodiment thereof.
Figure 2:
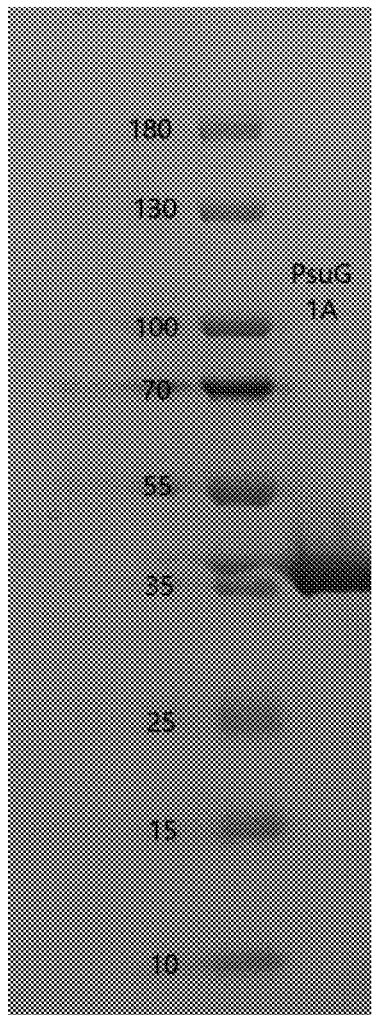
FIG. 2. shows expression and properties of recombinantly expressed pseudouridine glycosidase (PsuG) enzyme in one embodiment thereof.
Figure 3A:
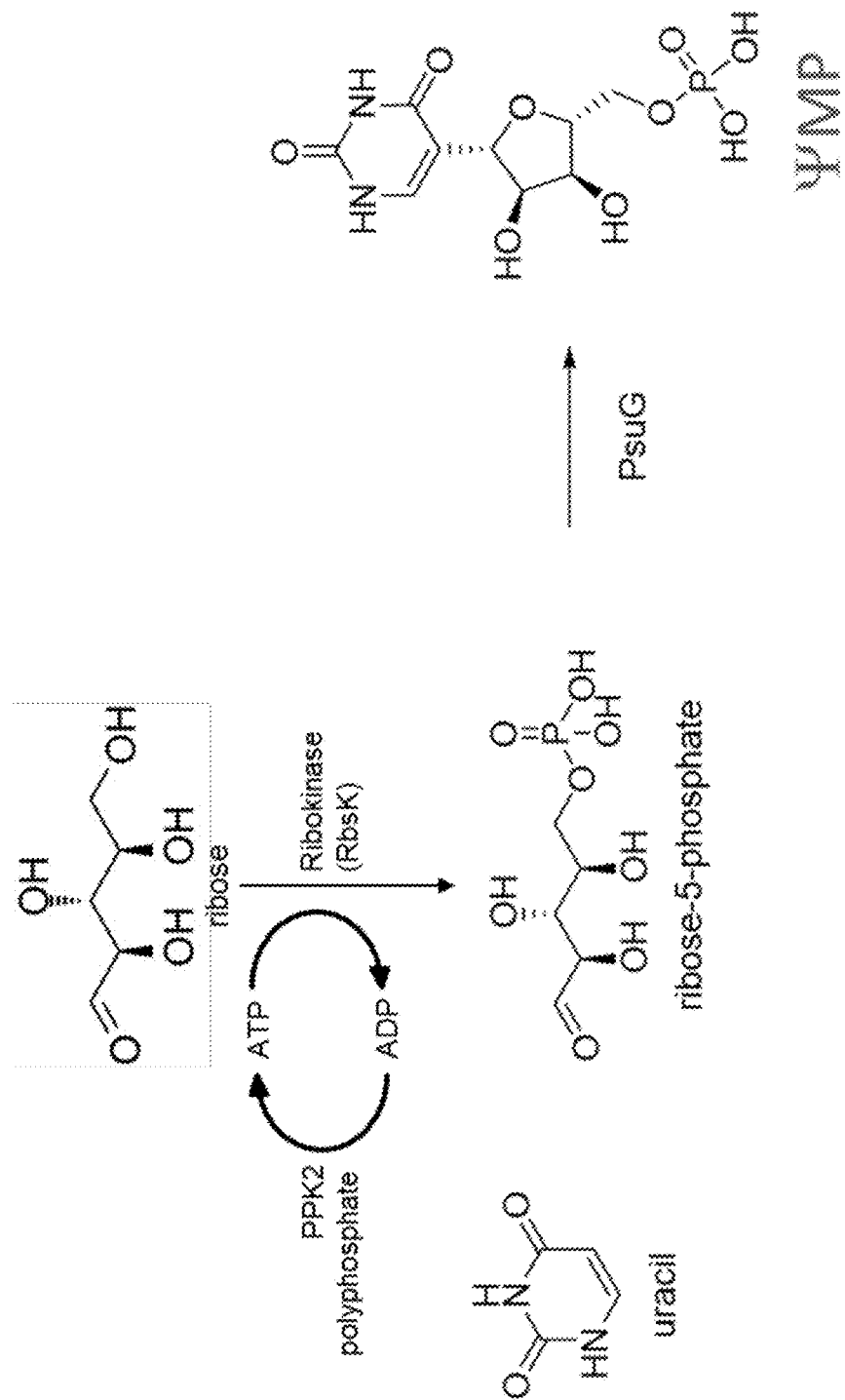
FIG. 3A-B. shows (A) a schematic scheme for the enzymatic production of uridine-5'-monophosphate (ΨMP) from uracil and ribose-5-phosphate catalyzed by the reverse reaction of PsuG in one embodiment thereof; (B) shown time-course production of ΨMP catalyzed by PsuG in one embodiment thereof.
Figure 3B:
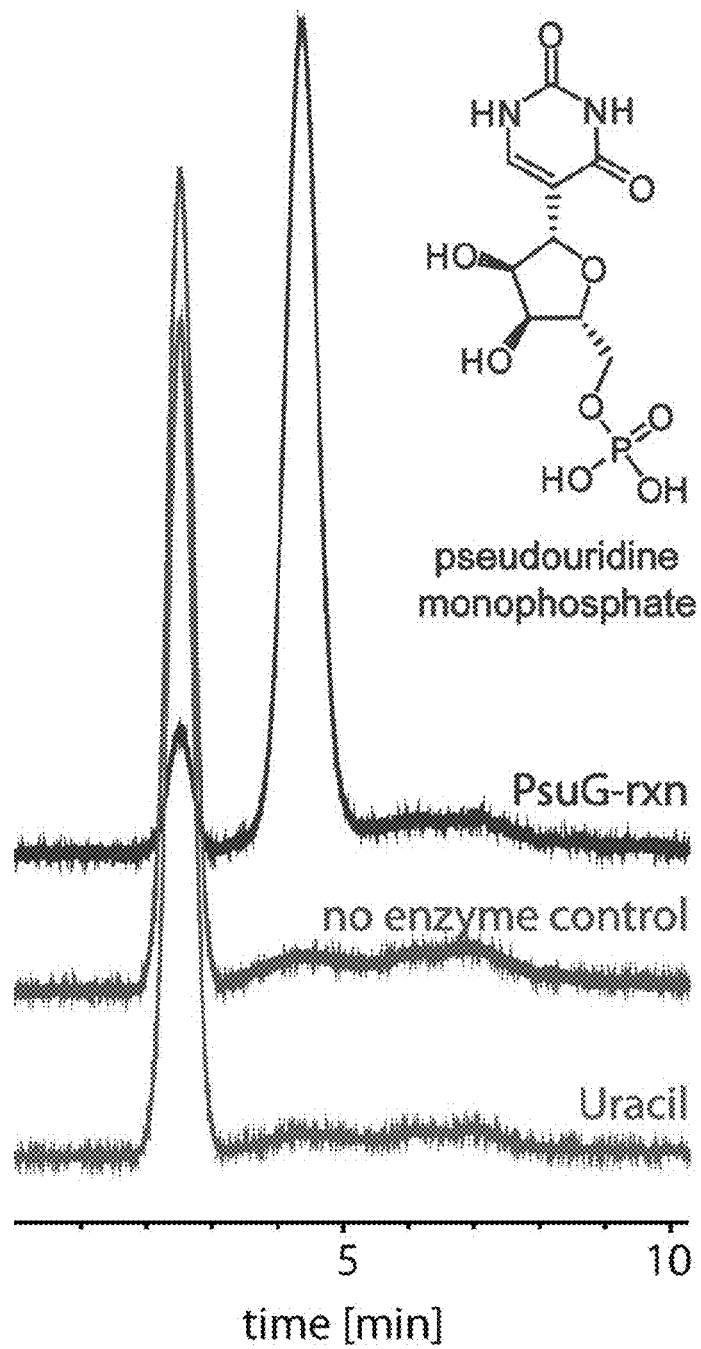
Figure 4A:
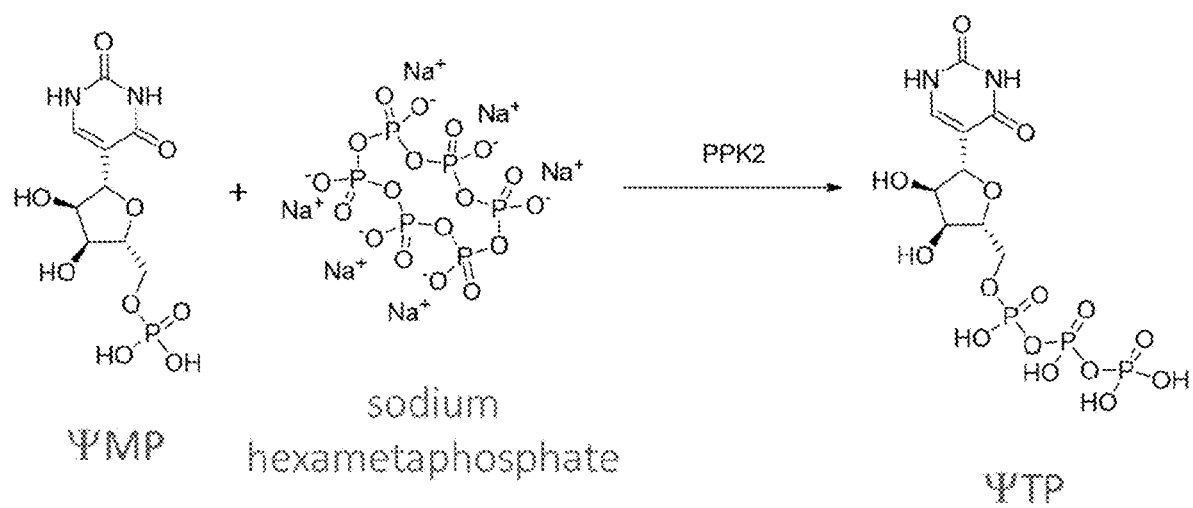
FIG. 4A-B. shows (A) a schematic scheme for the enzymatic regeneration of ΨTP from ΨMP using sodium hexametaphosphate catalyzed by deoxynucleoside kinase (PPK2) in one embodiment thereof; (B) the enzymatic regeneration of ΨTP from ΨMP using an enzymatic feedback loop of PPK2+inorganic polyphosphate and a nucleoside-diphosphate kinases (NdK) to regenerate ΨTP from ΨMP using an ATP donor, resulting in the production of AMP which is recycled back to ATP in one embodiment thereof.
Figure 4B:
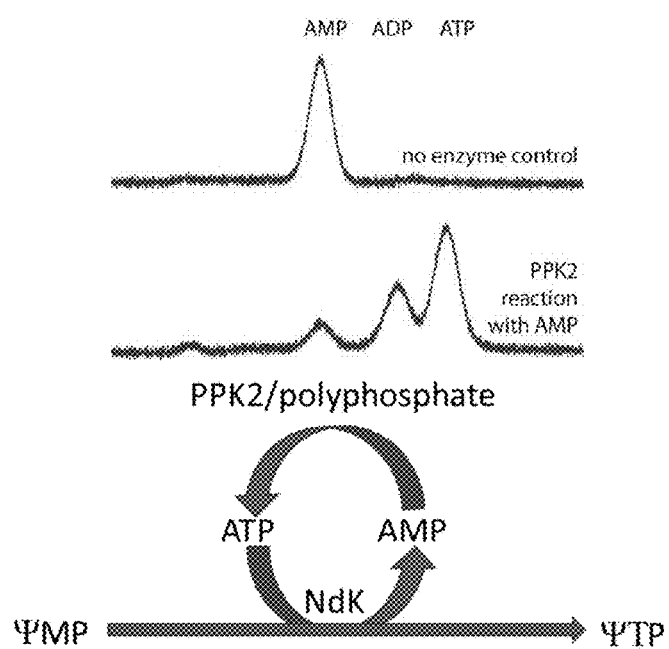

The present invention includes novel systems, methods, and compositions for the scalable enzymatic production of pUTP from uridine continuing RNA oligonucleotides, and preferably RNA oligonucleotides isolated from fermentation waste and other natural or synthetic sources. In a preferred embodiment, the invention may include generating a sample containing an RNA oligonucleotide, and preferably a plurality of RNA oligonucleotides isolated from fermentation waste, such as bacterial cultures grown in laboratories or macro-molecule production systems, or yeast waste products from the beer and wine fermentation industry, as well as yeast-based macro-molecule production systems and the like.

Preferably in an in vitro reaction chamber, such as a bio-chamber, an isolated pseudouridine synthase enzyme, or a fragment or variant thereof, may catalytically convert uridine nucleotide residues in the RNA oligonucleotides into Ψ residues. In a preferred embodiment, a pseudouridine synthase of the invention may selected from the group consisting of: SEQ ID NO's. PUS1-PUS9 (SEQ ID NO.'s 11-19), or a fragment or variant thereof. In the same or separate in vitro reaction chamber, an N1-pseudouridine methyltransferase, or a fragment or variant thereof, may further catalyze the methylation of the newly formed Ψ residues in the RNA oligonucleotides forming a series of N1-methyl-pseudouridine (m1Ψ) residues. In a preferred embodiment, N1-pseudouridine methyltransferase comprises Nep1 and more preferably may include a mNep1 enzyme according to SEQ ID NO. 8, or a fragment or variant thereof.

In another preferred embodiment, in the same or separate in vitro reaction chamber, an modified N1-pseudouridine methyltransferase (mNep1), or a fragment or variant thereof, may catalyze the methylation of the newly formed Ψ residues in the RNA oligonucleotides forming a series of N1-methyl-pseudouridine (m1Ψ) residues. In this embodiment, the 129R and 132R resides of Nep1 are converted to 129A and 132A forming mNep1 (SEQ ID NO. 9). These engineered mutations may allow the formation of individual m1Ψ residues from the Ψ residues of the RNA oligonucleotide by reducing the coordination of mNep1 with the nucleotide(s) adjacent to the Ψ residues in the RNA oligonucleotides.

The RNA oligonucleotide now containing a series of m1Ψ residues may be digested forming a plurality of nucleotide mono-phosphates, including m1Ψ-monophosphates (m1ΨMP). In a preferred embodiment, the RNA oligonucleotide may be digested with a nuclease P1, or 5'-Phosphodiesterase (5'-PDase), or a fragment or variant thereof. The resulting m1ΨMP can further be isolated and/or purified, for example through a weak anion exchange column, or other similar purification apparatus.

The enzymatically generated m1ΨMP may further be regenerated into their N1-methyl-pseudouridine-5'-triphosphate (m1ΨTP) form. In this preferred embodiment, a nucleoside diphosphate kinase (NdK), in the presence of an adenosine-triphosphate (ATP) donor, catalyzes the transfer of a phosphate group to the m1ΨMP, forming adenosine-monophosphate (AMP) while sequentially forming a m1Ψ-di-phosphate (m1ΨDP), and ultimately a pseudouridine-5'-triphosphate (m1ΨTP) that can be further isolated and/or purified. In one embodiment, the NdK of the invention may include an adenosyl kinase (AdK), and may preferably include an AdK according to: SEQ ID NO. 10, or a fragment or variant thereof.

The AMP resulting from the ATP donor of the invention may further be regenerated through the action of a polyphosphate kinase (PPK). In this embodiment, an AMP may be regenerated back into an ATP by the transfer of a inorganic polyphosphate to the AMP by a PPK enzyme. In a preferred embodiment, the PPK enzyme of the invention may include a PPK2 enzyme selected from the group consisting of: SEQ ID NO's. 4, 6, or a fragment or variant thereof. The regenerated ATP may be recycled back into the reaction cycle regenerating m1ΨTP from m1ΨMP.

As noted above, the above reactions may occur in vitro, separately or in the same or sequential in vitro reaction chambers. In a preferred embodiment, the above reactions may be performed in an in vitro transcription system, such as a cell-free expression system, or an in vitro RNA production system.

The present invention includes novel systems, methods, and compositions for the enzymatic production of Ψ derived from a uracil nucleobase and a ribose-5-phosphate. In a preferred embodiment, pseudouridine-5'-phosphate glycosidase (PsuG) enzyme may catalyze the formation of pseudouridine-5'-monophosphate (ΨMP) from the reversible reaction of two substrates, namely uracil nucleobase with a ribose-5-phosphate, preferably in an in vitro system, such as an in vitro transcription, or RNA production system. Substrate and temperature condition may be modulated to cause the reverse reaction of PsuG thereby catalyzing the formation ΨMP from the uracil nucleobase and ribose-5-phosphate substrates, where the normally forward reaction proceeds in the opposite direction catalyzing the cleavage of a ΨMP substrate to form a uracil nucleobase a ribose-5-phosphate product. In this embodiment, the revere reaction of PsuG may be facilitated by elevating the temperature of the reaction, for approximately 37° C. to 50° C., and increasing concentrations of both substrates, namely uracil and ribose-5-phosphate. In one embodiment, the concentrations of both uracil and ribose-5-phosphate may be at least 1 millimolar each. In this preferred embodiment, PsuG may be selected from a thermophilic bacteria, such as *D. geothermalis* (SEQ ID NO. 1, or 2) allowing the reaction to be run at a higher temperature, and preferably at least 50° C.

As noted above, the invention may include the generation of ΨTP from ΨMP by contacting the ΨMP with PPK2 in the present of an inorganic polyphosphate source, such as sodium hexamethaphosphate. In an alternative embodiment, the enzymatically produced ΨMP may be regenerated to form ΨTP through the catalytic action of a nucleoside diphosphate kinase (NdK) in the presence of an adenosine-triphosphate (ATP) donor, with the resulting ATP donor, now an AMP, being regenerated as described above.

The enzymatically created ΨTP may further be methylated by a N1-pseudouridine methyltransferase, or a fragment or variant thereof, forming N1-methyl-pseudouridine-5'-triphosphate (m1ΨTP). In a preferred embodiment, N1-pseudouridine methyltransferase includes Nep1 (SEQ ID NO. 8).

Figure 5:
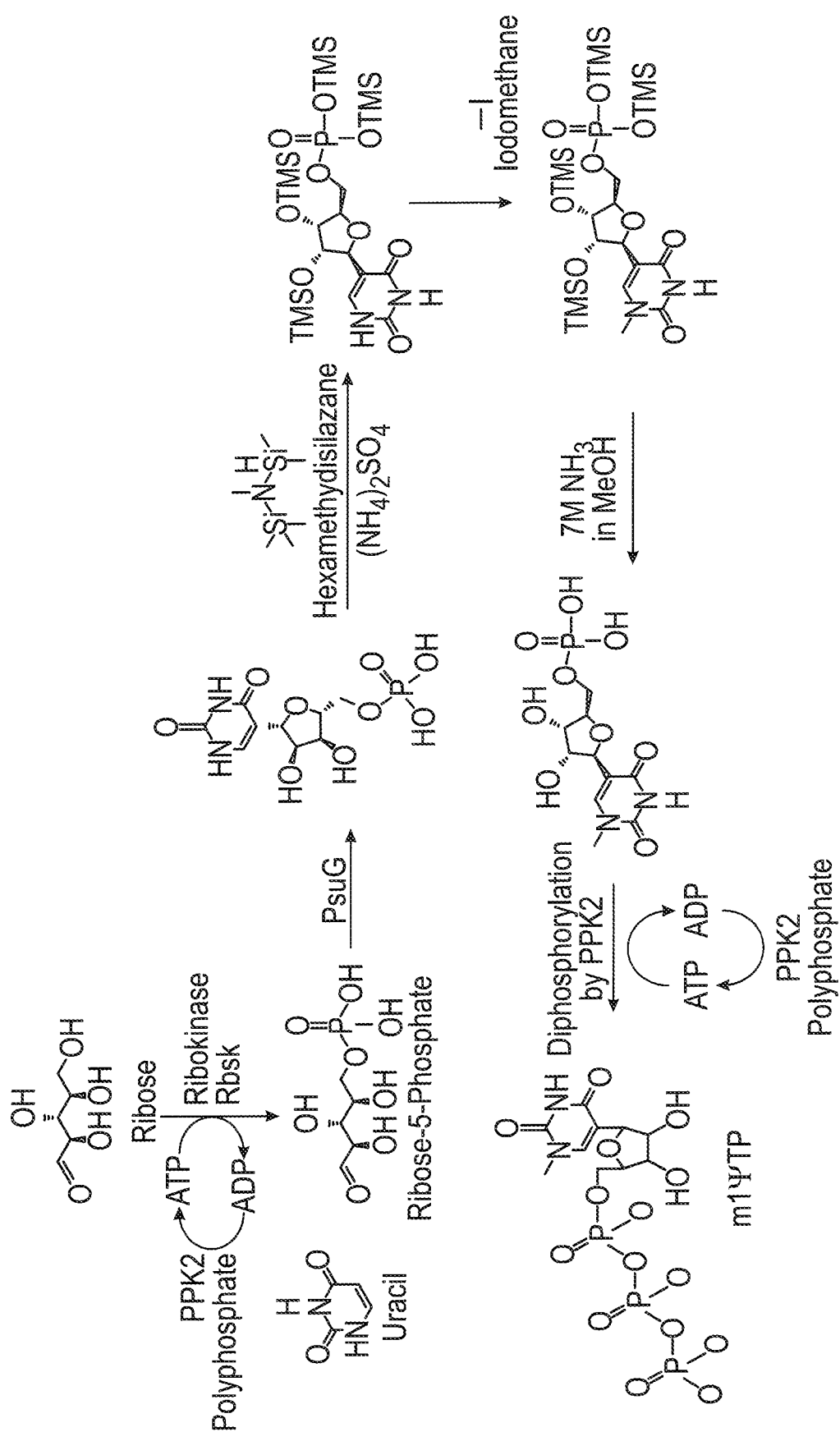
FIG. 5. show stepwise scheme 1 for the enzymatic and chemical production and m1ΨTP in one embodiment thereof.
Figure 6:
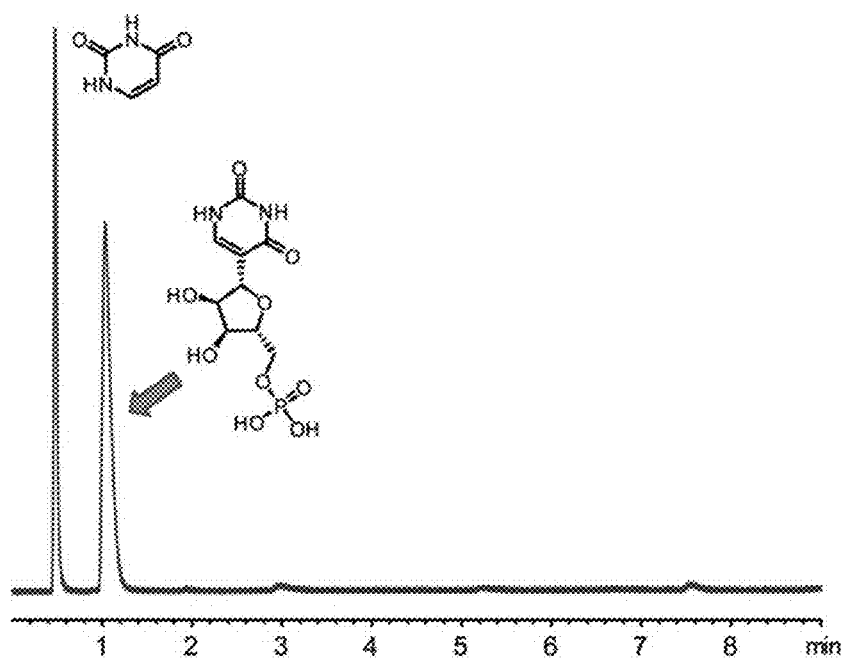
FIG. 6. shows enzymatic production of ΨMP using the scheme of FIG. 5, where ribose and polyP were dissolved in ~500 ml H2O and adjusted to pH 7 with the solution described in the Figure being fed into the reaction over ~20 hr.
Figure 7:
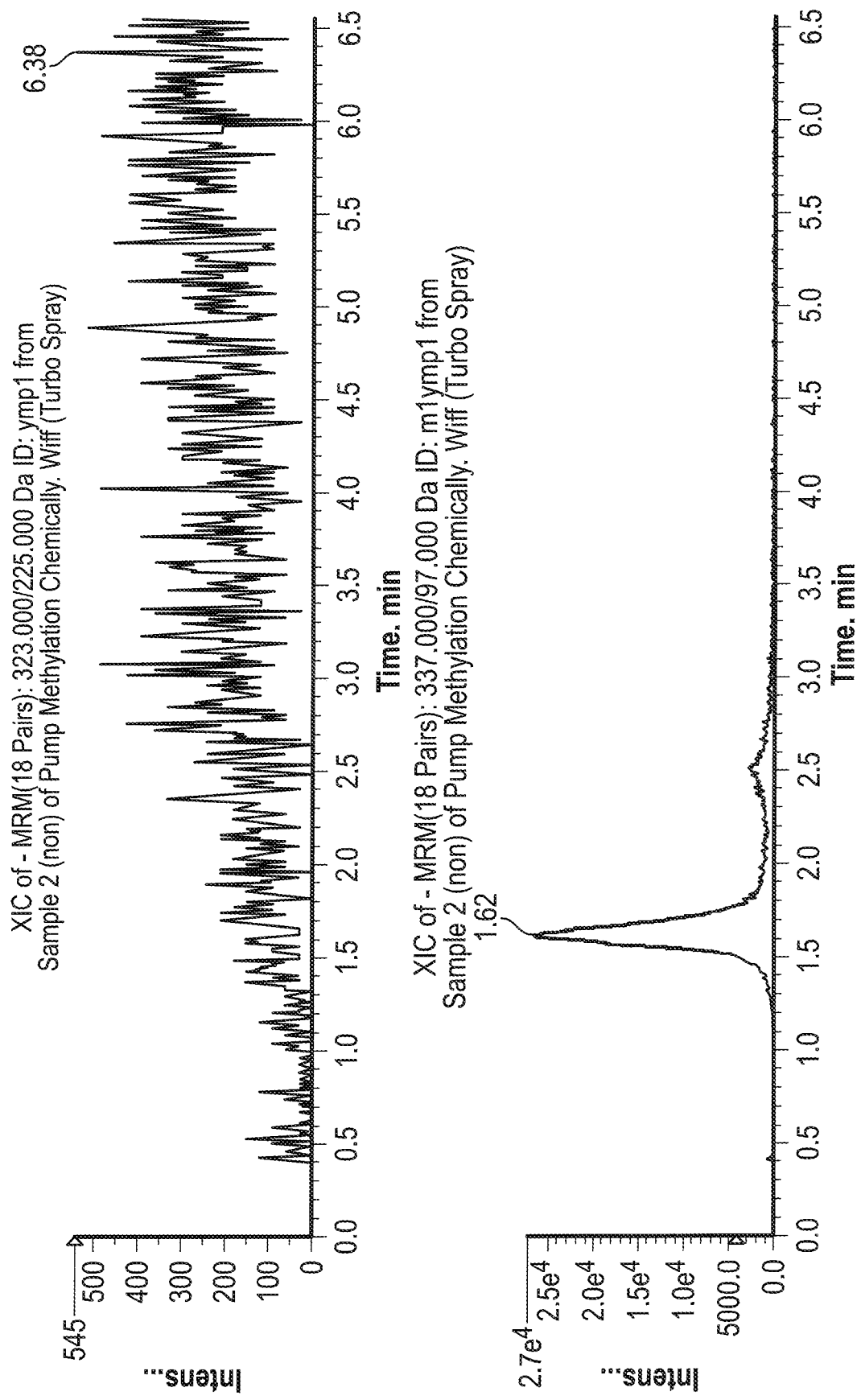
FIG. 7. demonstrates stepwise chemical methylation of ΨMP forming 1mΨMP. As shown in the Figures, small aliquot of chemical methylation reaction (200 mL) taken out after 36h, solvent removed under stream of nitrogen, deprotected using 300 mL of 7M $NH_3$ in MeOH, solvent removed again, dissolved in 500 mL of aq. 10 mM DBAA, 5 mL of that solution, subject to LC-MS analysis.
Figure 8:
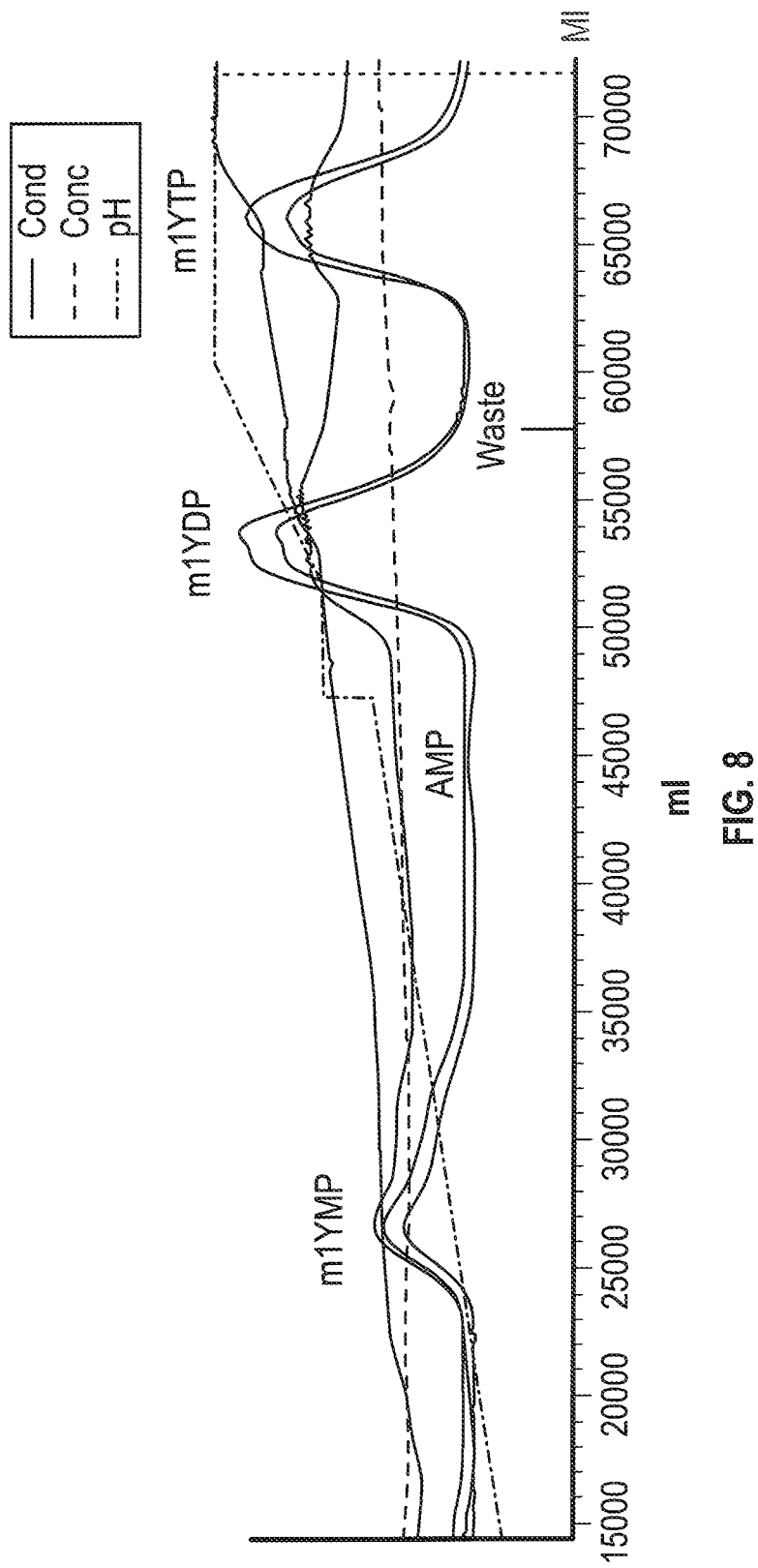
FIG. 8. shows enzymatic production of 1mΨTP from 1mΨMP. Reaction conditions included 25 mM 1mΨTP, 10 mM polyp, 0.25 mM PPK2, buffer: 50 mM HEPES, 25 mM $Mg^{2+}$, and 1 mM $Mn^{2+}$, at pH 7.
Figure 9A:
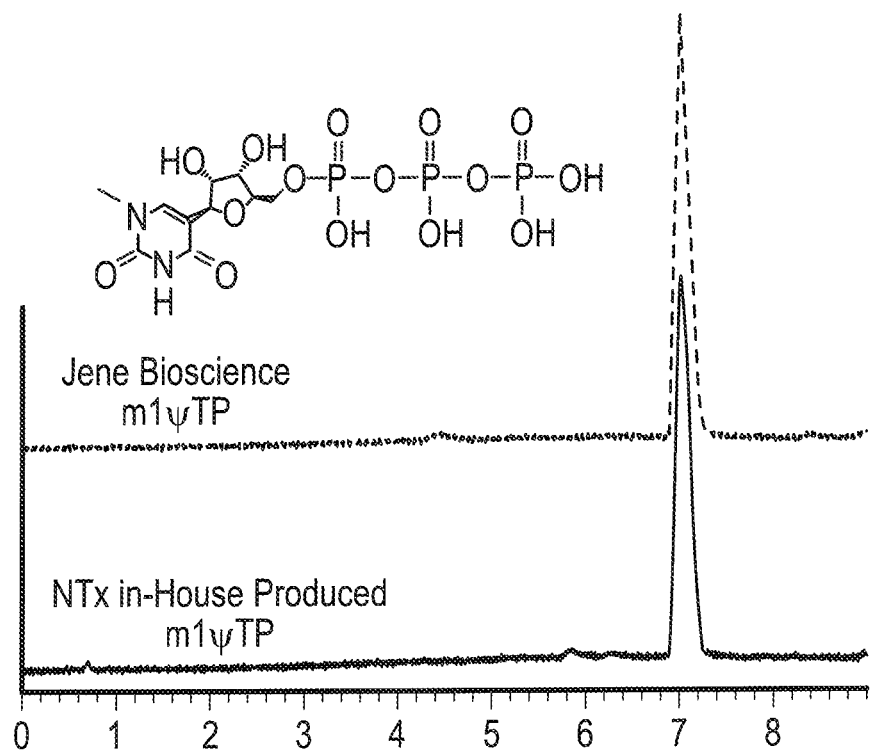
FIG. 9A-B. shows HPLC and MS analyses of purified 1mΨTP synthesized by scheme 1 as described herein.
Figure 9B:
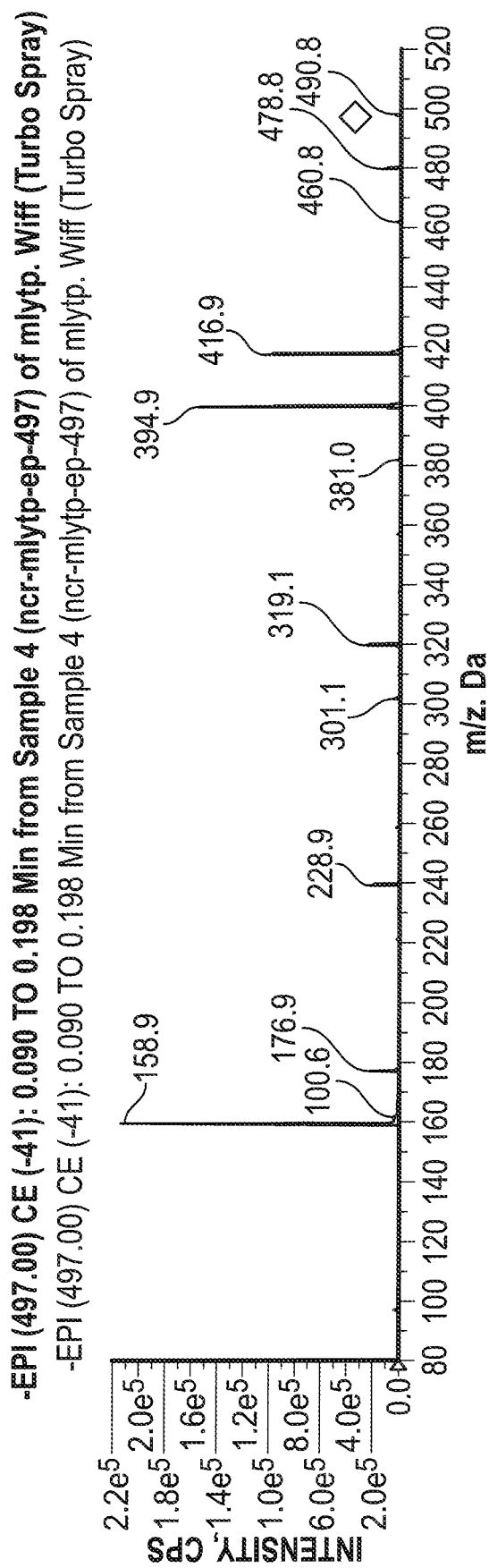
Figure 9B:
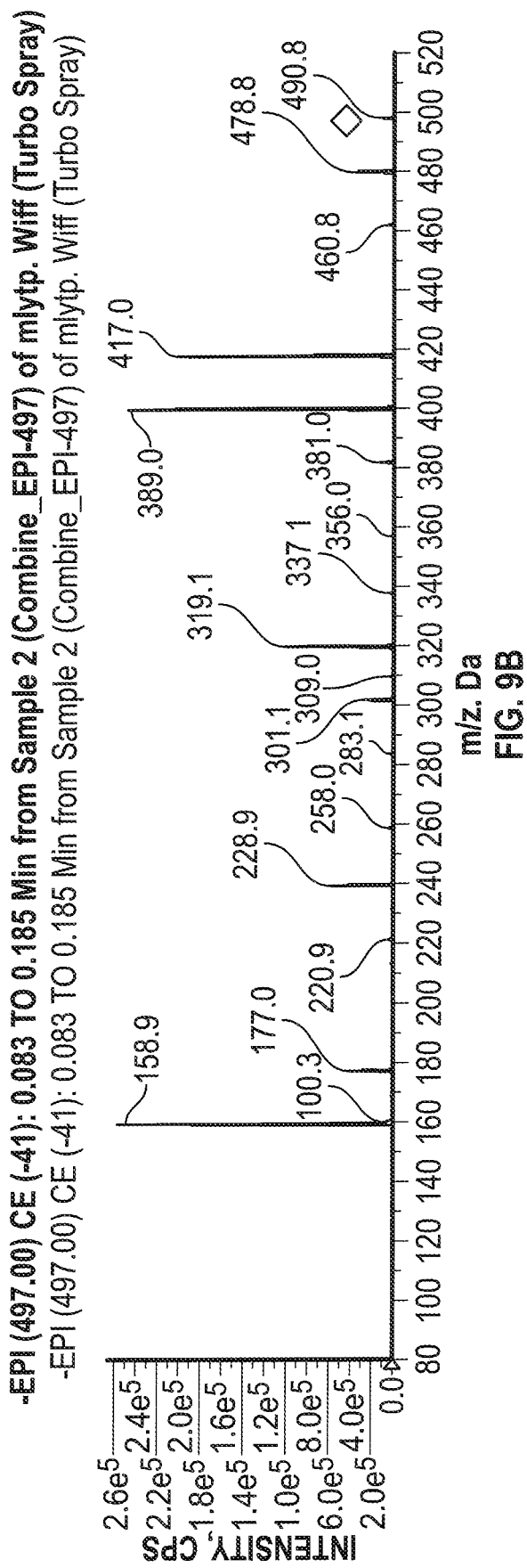
Figure 10:
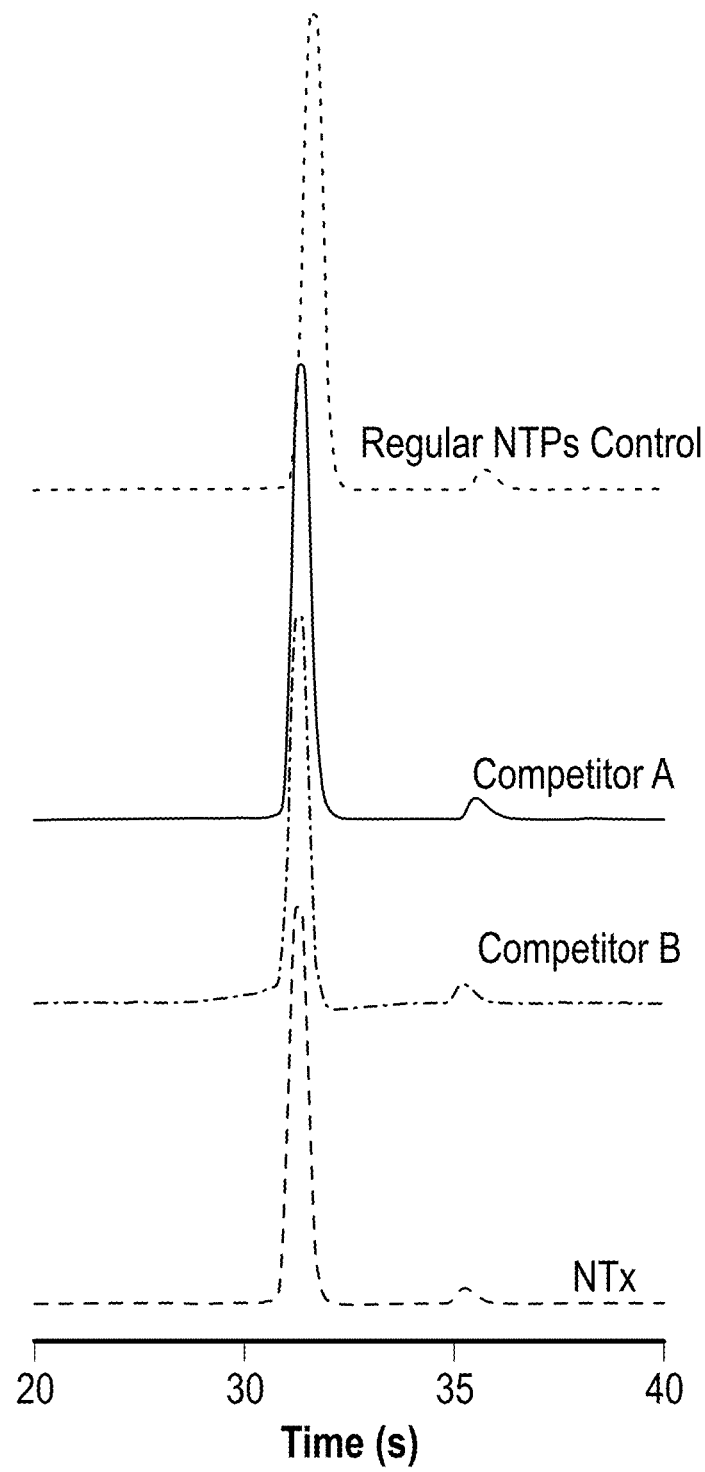
FIG. 10. shows in vitro transcription of RNA using 1mΨTP synthesized by scheme 1 as described herein as compared to commercially available transcription products.
Figure 11A:
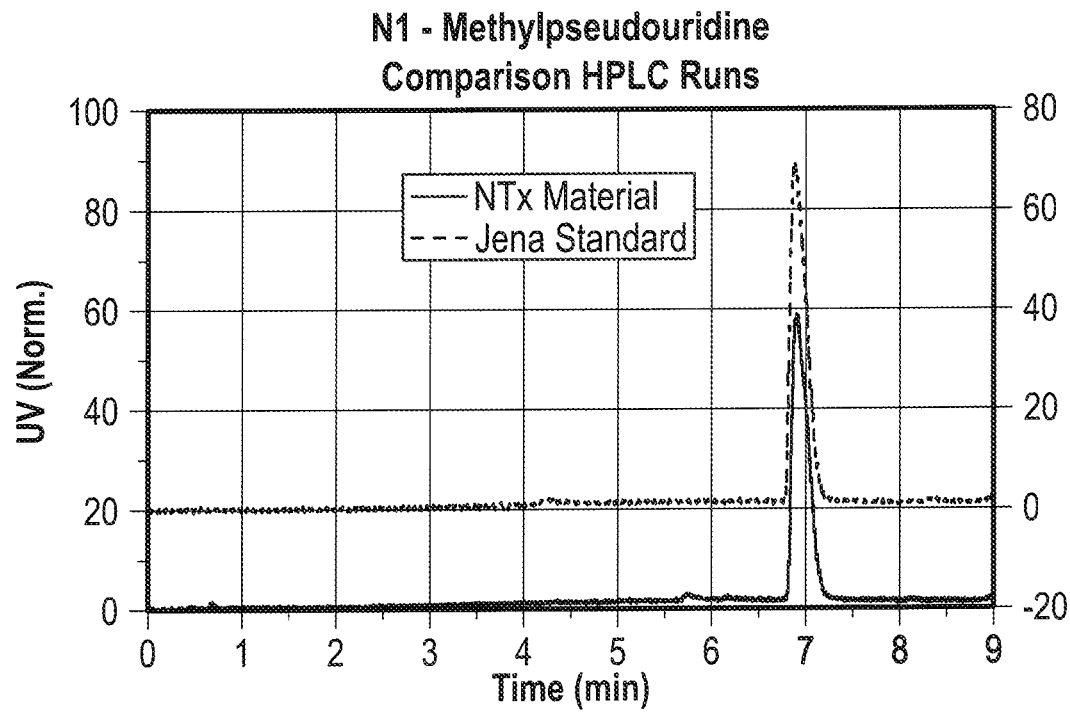
FIG. 11A-B. shows (A) HPLC analysis of m1Ψ run against standard (B) demonstrates HPLC analysis of the amounts and conversion of 1mΨTP, 1mΨDP and 1mΨMP from in vitro RNA transcription mixture.
Figure 11B:
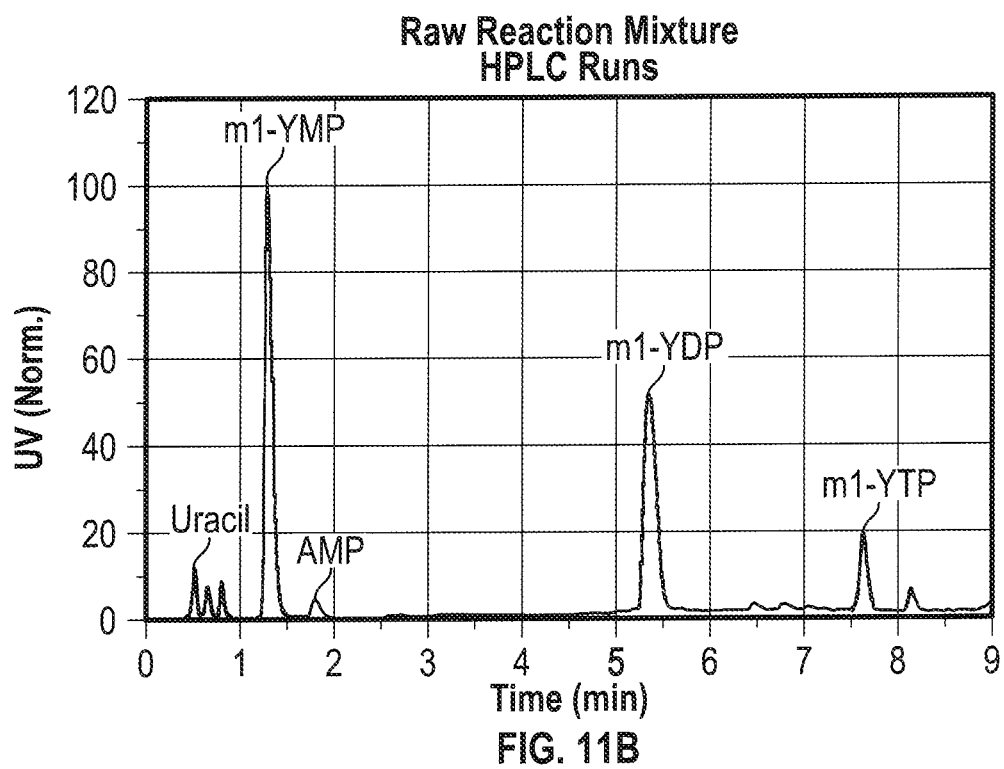
Figure 12A:
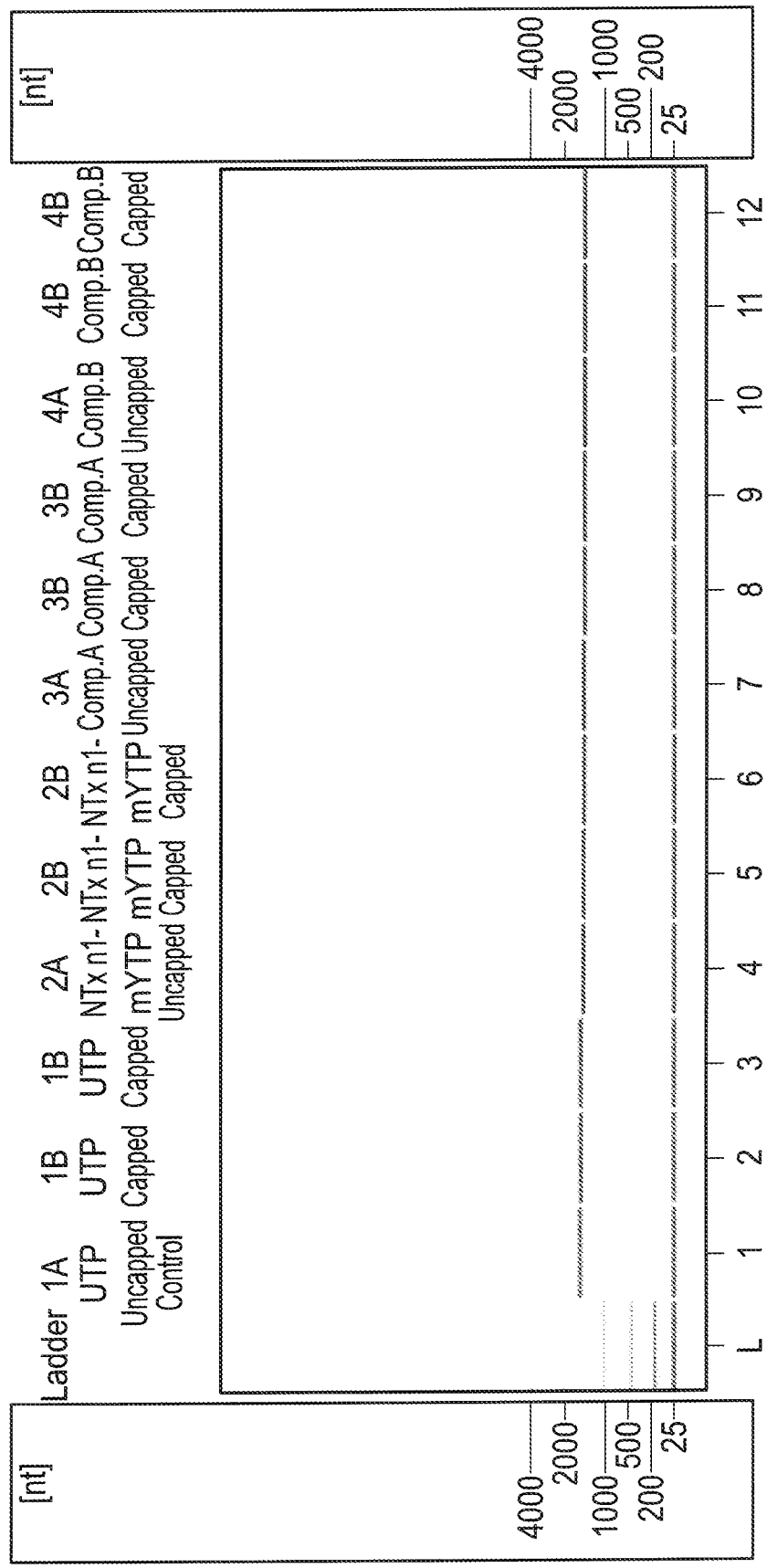
FIG. 12A-B. shows experimental results demonstrating enzymatic (A) capping and (B) tailing of mRNA transcripts utilizing N1-Methylpseudouridine generated by the method (s) of the invention in one embodiment thereof.
Figure 12B:
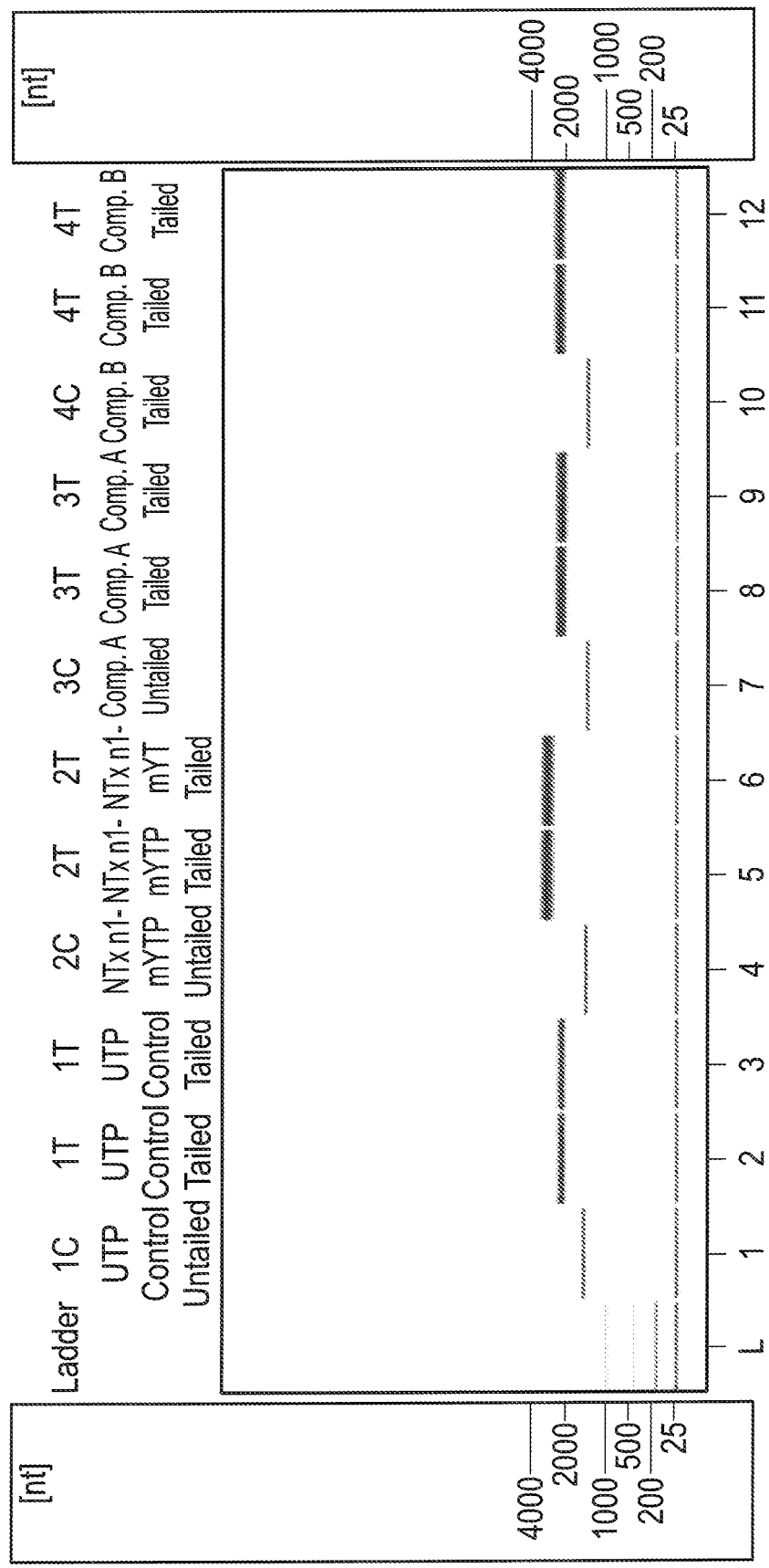

In one embodiment the invention includes systems, methods, and compositions for the enzymatic and chemical production of m1ΨTP, and preferably its use in an in vitro transcription reaction to generate RNA incorporating the same. Generally referring to the scheme provided in FIG. 5, invention can include the enzymatic synthesis of Ψ derived from a uracil nucleobase and a ribose-5-phosphate. In one embodiment, a Ribokinase (RbsK) enzyme can convert ribose to ribose-5-phosphate, with the phosphate group being donated from a molecule of ATP which is converted into ADP. As shown in FIG. 5, the ADP can be regenerated by reacting with a PPK enzyme in the presence of a polyphosphate forming ATP which can go on to be coupled to a ribose by RbsK forming ribose-5-phosphate. In a preferred embodiment, a Ribokinase (RbsK) enzyme according to the amino acid sequence SEQ ID NO. 20, or a fragment of variant thereof, can convert ribose to ribose-5-phosphate, with the phosphate group being donated from a molecule of ATP which is converted into ADP. Again, the resulting ADP can be regenerated by reacting with a PPK enzyme according to SEQ ID NO. 4, 6, 21, or a fragment of variant thereof, in the presence of a polyphosphate forming ATP which can go on to be coupled to a ribose by RbsK according to the amino acid sequence SEQ ID NO. 20, or a fragment of variant thereof, forming ribose-5-phosphate.

Again referring to synthesis scheme of FIG. 5, the present invention further includes novel systems, methods, and compositions for the enzymatic production of Ψ derived from a uracil nucleobase and a ribose-5-phosphate, preferably generated by the methods described above. In a preferred embodiment, a pseudouridine-5'-phosphate glycosidase (PsuG) enzyme may catalyze the formation of pseudouridine-5'-monophosphate (ΨMP) from the reversible reaction of two substrates, namely uracil nucleobase with a ribose-5-phosphate, preferably in an in vitro system, such as an in vitro transcription, or RNA production system. Substrate and temperature condition may be modulated to cause the reverse reaction of PsuG thereby catalyzing the formation ΨMP from the uracil nucleobase and ribose-5-phosphate substrates, where the normally forward reaction proceeds in the opposite direction catalyzing the cleavage of a ΨMP substrate to form a uracil nucleobase a ribose-5-phosphate product. In this embodiment, the reverse reaction of PsuG may be facilitated by elevating the temperature of the reaction, for approximately 37° C. to 50° C., and increasing concentrations of both substrates, namely uracil and ribose-5-phosphate. In one embodiment, the concentrations of both uracil and ribose-5-phosphate may be at least 1 millimolar each. In this preferred embodiment, PsuG may be selected from a thermophilic bacteria, such as *D. geothermalis*, and may include the amino acid sequence according to SEQ ID NO. 1, or 2, or a fragment of variant thereof. In this manner, the use of enzymes from thermophilic organisms allows the reaction to be run at a higher temperature, and preferably at least 50° C.

Again referring to the synthesis scheme of FIG. 5, the hydroxyl groups of the ΨMP substrate formed by a uracil nucleobase a ribose-5-phosphate is methylated to form m1ΨMP. In one embodiment, the hydroxyl groups of the ΨMP can react with a protecting agent, preferably an N-silyl compound, such as a quantity of hexamethyldisilazane (HMDS) generating a protecting group of trimethylsilyl ether (—OTMS) at the former hydroxyl position of the ΨMP, forming what is referred to herein as a protected ΨMP, according to the formula provided below:

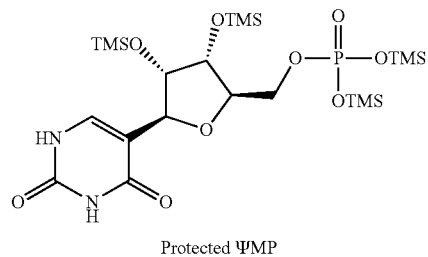

Protected ΨMP

The resulting protected ΨMP compound can react with a methylating agent so as to be methylated at the 1 position, forming a protected m1ΨMP compound. In a preferred embodiment, the protected m1ΨM is reacted with a quantity of a methylating agent, and preferably iodomethane that methylates the 1 position of the protected ΨMP, forming a protected m1ΨM according to the formula provided below:

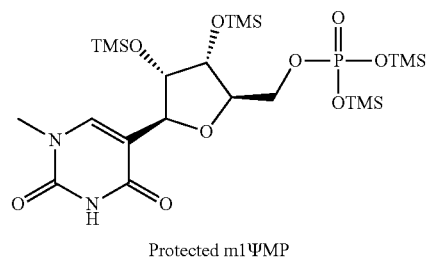

Protected m1ΨMP

The protected m1ΨMP compound of the invention can further be deprotected. In this embodiment, a deprotection agent can react with the protected m1ΨMP forming a m1ΨMP. In one embodiment, for example m1ΨMP with a deprotection agent that includes a quantity of ammonia in methanol. Removal of the protecting groups results in the formation of m1ΨMP.

In a preferred embodiment, the m1ΨMP synthesized by the proceeding steps can be enzymatically converted to m1ΨTP by diphosphorylation mediated by a phosphorylating agent, which in a preferred embodiment can includes a PPK enzyme, and preferably a PPK2 enzyme derived from thermophilic bacteria. Again referring to FIG. 5, a phosphate group from ATP is transferred to m1ΨMP, forming m1ΨDP, followed by the transfer of another phosphate group from an ATP to m1ΨDP, forming m1ΨTP respectively. In this preferred embodiment, the diphosphorylation is mediated by a PPK enzyme, and preferably a PPK2 enzyme to according to SEQ ID NO. 4, 6, 21, or a fragment of variant thereof.

In certain embodiment, the invention further include systems, methods and compositions for the production of heterologous proteins for use in the production of m1ΨTP. For example, in one embodiment, a cell, and preferably a yeast, bacterial or other prokaryotic cell can be transformed by an expression vector expressing one or more of the enzymes of the invention. In this embodiment, a cell can express a heterologous nucleotide, operably linked to a promoter, encoding a PsuG, and/or PPK2 protein, or a fragment of variant thereof of the invention. In another preferred embodiment, a cell, such as a yeast cell, can express a heterologous nucleotide, operably linked to a promoter, encoding a PsuG enzyme according to SEQ ID NO. 1, or 2, or a fragment of variant thereof, and/or PPK2 enzyme to according to SEQ ID NO. 4, 6, 21, or a fragment of variant thereof. In this preferred embodiment, the transformed yeast cell can be cultured and in a suitable media. Expression of the PsuG and/or PPK2 enzyme can occur, with the resulting proteins being actively or passively directed out of the yeast cell into the supernatant, from which they can be isolated.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g., a feature, element, characteristic, property, method/process step or limitation) or group of integers (e.g., features, element, characteristics, properties, method/process steps or limitations) but not the exclusion of any other integer or group of integers. Thus, as used herein the term "comprising" is inclusive or open-ended and does not exclude additional, unrecited integers or method/process steps.

The term "polynucleotide" or "nucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that is the basic structural unit of nucleic acids. The term "nucleoside" refers to a compound (such as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a with a different functional group. Accordingly, the term "polynucleotide" includes nucleic acids of any length, and in particular DNA, RNA, analogs and fragments thereof. A polynucleotide of three or more nucleotides is also called an "oligomer" or "oligonucleotide."

The term "messenger ribonucleic acid" (messenger RNA, mRNA) refers to a ribonucleic acid (RNA) molecule that mediates the transfer of genetic information to ribosomes in the cytoplasm, where it serves as a template for protein synthesis. It is synthesized from a DNA template during the process of transcription. A "ribonucleic acid" (RNA) is a polymer of nucleotides linked by a phosphodiester bond, where each nucleotide contains ribose or a modification thereof as the sugar component. Each nucleotide contains an adenine (A), a guanine (G), a cytosine (C), an uracil (U) or a modification thereof as the base. The genetic information in a mRNA molecule is encoded in the sequence of the nucleotide bases of the mRNA molecule, which are arranged into codons consisting of three nucleotide bases each. Each codon encodes for a specific amino acid of the polypeptide, except for the stop codons, which terminate translation (protein synthesis). Within a living cell, mRNA is transported to a ribosome, the site of protein synthesis, where it provides the genetic information for protein synthesis (translation). For a fuller description, see, Alberts B et al. (2007) *Molecular Biology of the Cell*, Fifth Edition, Garland Science.

As used herein, "in vitro transcription" (IVT) or "RNA production system" refers to a cell-free reaction in which a double-stranded DNA (dsDNA) template is copied by a DNA-directed RNA polymerase (typically a bacteriophage polymerase) to produce a product that contains RNA molecules copied from the template. An example of in vitro transcription may include cell-free expression systems that produce RNA transcripts or other macromolecules, such as peptides. In certain embodiments, the invention may encompass the in vitro production of artificial mRNA as well as wild-type mRNA. An artificial mRNA (sequence) may typically be understood to be an mRNA molecule, that does not occur naturally. In other words, an artificial mRNA molecule may be understood as a non-natural mRNA molecule. Such mRNA molecule may be non-natural due to its individual sequence (which does not occur naturally) and/or due to other modifications, e.g., structural modifications of nucleotides which do not occur naturally. Typically, artificial mRNA molecules may be designed and/or generated by genetic engineering methods to correspond to a desired artificial sequence of nucleotides (heterologous sequence). In this context an artificial sequence is usually a sequence that may not occur naturally, i.e., it differs from the wildtype sequence by at least one nucleotide. The term "wild type" may be understood as a sequence occurring in nature. Further, the term "artificial nucleic acid molecule" is not restricted to mean "one single molecule" but is, typically, understood to comprise an ensemble of identical molecules. Accordingly, it may relate to a plurality of identical molecules contained in an aliquot.

In certain embodiment, the invention may encompass the in vitro production of bi/multicistronic mRNA: mRNA, that typically may have two (bicistronic) or more (multi cistronic) open reading frames (ORF) (coding regions or coding sequences). An open reading frame in this context is a sequence of several nucleotide triplets (codons) that can be translated into a peptide or protein. Translation of such an mRNA yields two (bicistronic) or more (multi cistronic) distinct translation products (provided the ORFs are not identical). For expression in eukaryotes such mRNAs may for example comprise an internal ribosomal entry site (IRES) sequence.

In one embodiment, the in vitro produce mRNA configured to be translated to form a peptide, and preferably in a host organism, such as a mammal or human subject in need thereof. A peptide is a polymer of amino acid monomers. Usually, the monomers are linked by peptide bonds. The term "peptide" does not limit the length of the polymer chain of amino acids. In some embodiments of the present invention a peptide may for example contain less than 50 monomer units. Longer peptides are also called polypeptides, typically having 50 to 600 monomeric units, more specifically 50 to 300 monomeric units.

Additional examples of IVT systems, include in vitro recombinant cell-free expression systems, which refers to the cell-free synthesis of polypeptides in a reaction mixture or solution comprising biological extracts and/or defined cell-free reaction components, such as the exemplary system described by Koglin et al., in PCT/US2020/028005 and PCT/US2021/027774 (incorporated herein by reference). The reaction mixture may optionally comprise a template, or genetic template, for production of the macromolecule, e.g., DNA, mRNA, etc.; monomers for the macromolecule to be synthesized, e.g., amino acids, nucleotides, etc.; and such co-factors, enzymes and other reagents that are necessary for the synthesis, e.g., ribosomes, tRNA, polymerases, transcriptional factors, etc. The recombinant cell-free synthesis reaction, and/or cellular adenosine triphosphate (ATP) energy regeneration system components, incorporated by reference herein, may be performed/added as batch, continuous flow, or semi-continuous flow.

Examples of in vitro production systems have been also previously described in the art, including U.S. Pat. No. 11,136,586, and PCT Application No. PCT/US2020/028005. The disclosed methods and conditions for the production of synthetic RNAs in each of the aforementioned references, including the methods, systems and compositions outline in the claims, Examples and Materials and Methods is hereby incorporated in their entirety by reference. For example, a synthetic RNA oligonucleotide may be generated and capped within a Cell Free (CF) expression system. In one embodiment, a CF expression system may include a fully recombinant stable, reliable, and functional in vitro transcription system for the continuous flow production of RNA. As noted above, an exemplary CF system being generally described by A. Koglin and M. Humbert et al., in PCT/US2018/0121121, and PCT/US2021/027774 (previously identified as incorporated by reference) may be used as an in vitro platform to produce synthetic mRNAs. As noted in the art, lysate-based in vitro systems are challenged by limited stability of typical *E. coli* enzymes, by the activity of most metabolic processes (nucleotide recycling) and the presence of nucleases and proteases and insufficient ATP regeneration. Utilizing the CF system described by Koglin and Humbert, and using only components: linear DNA template, an affinity-tagged RNA polymerase, nucleotides in a defined buffer system, and a capping enzyme of the invention, the in vitro synthesis of the mRNA may be performed in hollow fiber reactors using a continuous flow system, as well as other traditional bioreactors known in the art. Using this in vitro system, the inner chamber (hollow fibers) of the bioreactor provides additional nucleotides in flow, the outer chamber holds the RNA polymerase and each linear DNA template. In this setup, the present inventors demonstrate that the total turnover of the RNAP is at least 50 fold higher than in batch reaction and, coupled with modifications to selected enzyme, produce cleaner mRNA without smear. All enzymes are engineered with an affinity tag, to allow the whole reaction to be washed through a bed of affinity resin, which is partially loaded with DNase to remove the template and to capture the RNA polymerase. In this way the process avoids the need to address phenol precipitations and spin column purifications (which is still an issue with traditional vaccine processes). In this system, the leaching or carryover of components from the RNA biosynthesis may be the mid ppb range. After a scalable and simple precipitation and drying process, the resulting mRNA is stable as a powder and does not contain traces of any components from the manufacturing process. It is ready to ship requiring only reduced volumes without the needed of hard-to-monitor and expensive shipping conditions.

In some embodiments the IVT of the invention may include a "bioreactor" that may be any form of enclosed apparatus configured to maintain an environment conducive to the production of macromolecules in vitro. A bioreactor may be configured to run on a batch, continuous, or semi-continuous basis, for example by a feeder reaction solution. Examples of a bioreactor and conditions for synthesis of RNA or other macromolecules has been previously described in by Koglin, et al. PCT/US2021/027774.

The terms "isolated", "purified", or "biologically pure" as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high-performance liquid chromatography. A nucleic acid or particular bacteria that are the predominant species present in a preparation is substantially purified. In an exemplary embodiment, the term "purified" denotes that a nucleic acid or protein that gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. As used herein "protecting group" means an atomic group that, when attached to a reactive functional group in a molecule, masks, reduces or prevents the reactivity of the functional group. Non-limiting examples of protecting groups may be found in "Protective Groups in Organic Chemistry", T. W. Greene, P. G. M. Wuts, ISBN 0-471-62301-6, John Wiley & Sons, Inc, New York. A "deprotecting agent," is any compound, or mixture of compounds that removes a protecting group.

In a preferred embodiment, a protecting group can include hydroxy "protecting group," which can be any protecting group suitable for a hydroxy functional group. Representative hydroxy protecting groups include, but are not limited to, silanes, ethers, esters, or others. Representative hydroxy protecting groups include, but are not limited to hexamethyldisilazane (HMDS), trimethyl silane (TMS), t-butyl dimethyl silane (TBDMS), t-butyl diphenyl silane (TBDPS), methoxy-methyl (MOM), tetrahydropyran (THP), t-butyl, allyl, benzyl, acetyl, pivaloyl, or benzoyl. In some embodiments, the hydroxy protecting group can be trimethyl silane (TMS), t-butyl dimethyl silane (TBDMS), t-butyl diphenyl silane (TBDPS), methyl-methoxy (MOM), tetrahydropyran (THP), t-butyl, allyl, benzyl, acetyl, pivaloyl, or benzoyl. In some embodiments, the hydroxy protecting group can be benzyl. In some embodiments, the hydroxy protecting group can be TBS.

"Methylating agent" means a reactive species, having electrophilic properties, which is capable of introducing a "methyl group" at the nitrogen atom of naltrexone, so as to form a covalent bond therewith. Illustrative methylating agents can be represented by the formula CH3Z, wherein "Z" is a leaving group which, upon its departure, enables CH3 to form a covalent bond with the nitrogen atom of naltrexone, forming MNTX. Methylating agents in general, and leaving groups in general, are well known to those of ordinary skill in the art and are described extensively in both the patent literature and in chemistry text books. Suitable Z groups include, but are not limited to, fluoro, chloro, bromo, iodo, iodomethane, —OSO2CF3, CH3OSO2O—, —OSO2CH3, —OSO2C6H4-p-CH3, —OSO2C6H4-p-Br.

As the phosphorylating agent, means reagents or enzymes that are generally used in the phosphorylation of a hydroxyl group. Examples of such phosphorylating agent compounds include diesters of phosphoric acid such as dibenzyl phosphate and the like; dithioesters of phosphoric acid such as monocyclohexylammonium S,S'-diphenylphosphoro dithioate and the like; phosphoric acid chlorides such as phosphoryl chloride, diallyl chlorophosphonate and the like. As additives, for example, azo compounds such as diethyl azodicarboxylate, diisopropyl azodicarboxylate and the like; phosphines such as triphenylphosphine and the like; allenesulfonic acid chlorides such as 2,4,6-triisopropylbenzenesulfonic acid chloride and the like, bases such as pyridine, tert-butylmagnesium chloride and the like can be referred to. Examples of such phosphorylating agents can also refer to enzymes, such as PPK2.

In preferred embodiments, the output of the cell-free expression system may be a product, RNA, or other macromolecule such as a peptide or fragment thereof that may be isolated or purified. In this embodiment, solation or purification of a of a target protein wherein the target protein is at least partially separated from at least one other component in the reaction mixture, for example, by organic solvent precipitation, such as methanol, ethanol or acetone precipitation, organic or inorganic salt precipitation such as trichloroacetic acid (TCA) or ammonium sulfate precipitation, nonionic polymer precipitation such as polyethylene glycol (PEG) precipitation, pH precipitation, temperature precipitation, immunoprecipitation, chromatographic separation such as adsorption, ion-exchange, affinity and gel exclusion chromatography, chromatofocusing, isoelectric focusing, high performance liquid chromatography (HPLC), gel electrophoresis, dialysis, microfiltration, and the like.

The term "nucleic acid" as used herein refers to a polymer of ribonucleotides or deoxyribonucleotides. Typically, "nucleic acid" polymers occur in either single- or double-stranded form but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, and peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein. For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

As is known in the art, different organisms preferentially utilize different codons for generating polypeptides. Such "codon usage" preferences may be used in the design of nucleic acid molecules encoding the proteins and chimeras of the invention in order to optimize expression in a particular host cell system. All nucleotide sequences described in the invention may be codon optimized for expression in a particular organism, or for increases in production yield. Codon optimization generally improves the protein expression by increasing the translational efficiency of a gene of interest. The functionality of a gene may also be increased by optimizing codon usage within the custom designed gene. In codon optimization embodiments, a codon of low frequency in a species may be replaced by a codon with high frequency, for example, a codon UUA of low frequency may be replaced by a codon CUG of high frequency for leucine. Codon optimization may increase mRNA stability and therefore modify the rate of protein translation or protein folding. Further, codon optimization may customize transcriptional and translational control, modify ribosome binding sites, or stabilize mRNA degradation sites.

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). In addition to the degenerate nature of the nucleotide codons which encode amino acids, alterations in a polynucleotide that result in the production of a chemically equivalent amino acid at a given site, but do not affect the functional properties of the encoded polypeptide, are well known in the art. "Conservative amino acid substitutions" are those substitutions that are predicted to interfere least with the properties of the reference polypeptide. In other words, conservative amino acid substitutions substantially conserve the structure and the function of the reference protein. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine or histidine, can also be expected to produce a functionally equivalent protein or polypeptide. Exemplary conservative amino acid substitutions are known by those of ordinary skill in the art. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain. Further disclosure of a nucleotide sequence, specifically includes the resulting amino acid sequence for which it encodes and vice versa.

As used herein, the term "transformation" or "genetically modified" refers to the transfer of one or more nucleic acid molecule(s) into a cell, preferably through an expression vector. A microorganism is "transformed" or "genetically modified" by a nucleic acid molecule transduced into the bacteria or cell or organism when the nucleic acid molecule becomes stably replicated. As used herein, the term "transformation" or "genetically modified" encompasses all techniques by which a nucleic acid molecule can be introduced into a cell or organism, such as a bacteria.

As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell.

The term "operably linked," when used in reference to a regulatory sequence and a coding sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor or binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

The term "expression," as used herein, or "expression of a coding sequence" (for example, a gene or a transgene) refers to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

An "expression vector" is nucleic acid capable of replicating in a selected host cell or organism, or in vitro environment, such as a cell-free expression system or other IVT system. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette." In contrast, as described in the examples herein, a "cassette" is a polynucleotide containing a section of an expression vector of this invention. The use of the cassettes assists in the assembly of the expression vectors. An expression vector is a replicon, such as plasmid, phage, virus, chimeric virus, or cosmid, and which contains the desired polynucleotide sequence operably linked to the expression control sequence(s).

The terms "expression product" as it relates to a protein expressed in a cell-free expression system as generally described herein, are used interchangeably and refer generally to any peptide or protein having more than about 5 amino acids. The polypeptides may be homologous to, or may be exogenous, meaning that they are heterologous, i.e., foreign, to the organism from which the cell-free extract is derived, such as a human protein, plant protein, viral protein, yeast protein, etc., produced in the cell-free extract.

In some embodiments, the term a nucleic acid or peptide may be from a source, such as a virus. In this context a "derived" nucleic acid, such as RNA, or peptide means extracted from, or expressed and isolated from a bacteria, eukaryotic cell or other source, such as fermentation waste. For example, in one embodiment a capping protein may be derived from an expression vector expressed in a bacteria, or eukaryotic cell.

As used herein, "RNA sample" or "sample" refers to a composition that contain one, or a plurality of oligonucleotides containing uridine residues. An RNA sample may comprise a naturally occurring RNA (e.g., extracted from a cell, tissue, or organism), a RNA produced by in vitro transcription, and/or a chemically synthesized RNA, or an RNA sample harvest from fermentation waste culture, and/or cells.

As used herein, "variant" refers to a protein that has an amino acid sequence that is different from a naturally occurring amino acid sequence (i.e., having less than 100% sequence identity to the amino acid sequence of a naturally occurring protein) but that is at least 80%, at least 85%, at least 90%, at least 95%, at least 97%, at least 98% or at least 99% identical to the naturally occurring amino acid sequence.

As used herein, "fragment" refers to a portion of a peptide or nucleotide sequence that still retains the activity of the whole.

Unless other stated, disclosure of a DNA sequence also include the corresponding RNA and amino acid sequence including all redundant codons and conservative amino acid substitutions, disclosure of a RNA sequence also include the corresponding DNA and amino acid sequence including all redundant codons and conservative amino acid substitutions, and finally disclosure of amino acid sequence also include the corresponding RNA and DNA sequence including all redundant codons and conservative amino acid substitutions and vice versa.

Additional Embodiments

In one preferred embodiment, the invention includes a method producing pseudouridine comprising:
- establishing a sample containing an RNA oligonucleotide;
- contacting said RNA oligonucleotide with a pseudouridine synthase or a fragment or variant thereof, converting one or more uridine nucleotide residues in said RNA oligonucleotide into one or more pseudouridine residues;
- contacting said pseudouridine residues with a N1-pseudouridine methyltransferase, or a fragment or variant thereof, forming N1-methyl-pseudouridine (m1Ψ) residues;
- digesting said RNA oligonucleotide containing the m1Ψ residues forming nucleotide mono-phosphates, including m1Ψ-monophosphate (m1ΨMP);
- isolating the m1ΨMP from said sample; and
- optionally regenerating pseudouridine-5'-triphosphate (m1ΨTP) from said m1ΨMP.

In another preferred embodiment, the invention includes a method producing pseudouridine wherein the step of establishing comprises isolating said RNA oligonucleotide.

In another preferred embodiment, the invention includes a method producing pseudouridine wherein said step of isolating comprises the step of isolating a quantity of RNA oligonucleotides from fermentation waste.

In another preferred embodiment, the invention includes a method producing pseudouridine wherein said fermentation waste is selected from the group consisting of: bacterial culture waste, yeast culture waste, and food and/or beverage fermentation waste.

In another preferred embodiment, the invention includes a method producing pseudouridine wherein said pseudouridine synthase is selected from the group consisting of: SEQ ID NO's. 11-19, or a fragment or variant thereof.

In another preferred embodiment, the invention includes a method producing pseudouridine wherein said N1-pseudouridine methyltransferase comprises Nep1 or a fragment or variant thereof.

In another preferred embodiment, the invention includes a method producing pseudouridine wherein said Nep1 comprises a peptide according to SEQ ID NO. 8, or a fragment or variant thereof.

In another preferred embodiment, the invention includes a method producing pseudouridine wherein said N1-pseudouridine methyltransferase comprises a modified N1-pseudouridine methyltransferase (mNep1).

In another preferred embodiment, the invention includes a method producing pseudouridine wherein said modified mNep1 comprises a modified mNep1 wherein 129R and 132R are converted to 129A and 132A.

In another preferred embodiment, the invention includes a method producing pseudouridine wherein said modified N1-pseudouridine methyltransferase comprises a peptide according to SEQ ID NO. 9, or a fragment or variant thereof.

In another preferred embodiment, the invention includes a method producing pseudouridine wherein said step of digesting comprises digesting said RNA oligonucleotide with nuclease P1, or 5'-Phosphodiesterase (5'-PDase), or a fragment or variant thereof.

In another preferred embodiment, the invention includes a method producing pseudouridine wherein said step of isolating comprises purifying m1ΨMP.

In another preferred embodiment, the invention includes a method producing pseudouridine wherein said step of purifying m1ΨMP comprises purifying m1ΨMP with a weak anion exchange column.

In another preferred embodiment, the invention includes a method producing pseudouridine wherein said step of regenerating comprises the step of contacting said m1ΨMP with a nucleoside diphosphate kinase (NdK) in the presence of an adenosine-triphosphate (ATP) donor.

In another preferred embodiment, the invention includes a method producing pseudouridine wherein said NdK is an adenosyl kinase (AdK) according to: SEQ ID NO. 10, or a fragment or variant thereof.

In another preferred embodiment, the invention includes a method producing pseudouridine further comprising the step of isolating said m1ΨTP.

In another preferred embodiment, the invention includes a method producing pseudouridine further comprising the step of regenerating said ATP donor by contacting adenosine-monophosphate (AMP) is a Polyphosphate kinase (PPK) or enzyme in the presence of inorganic polyphosphate.

In another preferred embodiment, the invention includes a method producing pseudouridine wherein said PPK2 is selected from the group consisting of: SEQ ID NO's. 4, 6, 21 or a fragment or variant thereof.

In another preferred embodiment, the invention includes a method producing pseudouridine wherein one or more of said steps of the invention, are performed in an in vitro transcription system.

In another preferred embodiment, the invention includes a method producing pseudouridine wherein said step of regenerating is performed in an in vitro transcription system.

In another preferred embodiment, the invention includes a method producing pseudouridine wherein said in vitro transcription system comprises an in vitro RNA production system.

In one preferred embodiment, the invention includes a system for producing pseudouridine comprising:
- a sample containing a quantity RNA oligonucleotides;
- a pseudouridine synthase enzyme or a fragment or variant thereof, that converts one or more uridine nucleotide residues in said RNA oligonucleotide unto one or more pseudouridine residues;
- a N1-pseudouridine methyltransferase enzyme, or a fragment or variant thereof, that methylates said pseudouridine residues forming N1-methyl-pseudouridine (m1Ψ) residues;
- a nuclease enzyme that digests said RNA oligonucleotide containing the m1Ψ residues forming nucleotide monophosphates, including m1Ψ-monophosphate (m1ΨMP).
- a nucleoside diphosphate kinase (NdK) and adenosine-triphosphate (ATP) donor that regenerates pseudouridine-5'-triphosphate (m1ΨTP) from said m1ΨMP.

In another preferred embodiment, the invention includes a system for producing pseudouridine wherein said sample containing a quantity RNA oligonucleotides comprises an isolated sample containing a quantity RNA oligonucleotides.

In another preferred embodiment, the invention includes a system for producing pseudouridine wherein the isolated sample comprises an isolated sample from fermentation waste.

In another preferred embodiment, the invention includes a system for producing pseudouridine wherein said fermentation waste is selected from the group consisting of: bacterial culture waste, yeast culture waste, and food and/or beverage fermentation waste.

In another preferred embodiment, the invention includes a system for producing pseudouridine wherein said pseudouridine synthase is selected from the group consisting of: SEQ ID NO's. 11-19 or a fragment or variant thereof.

In another preferred embodiment, the invention includes a system for producing pseudouridine wherein said N1-pseudouridine methyltransferase comprises Nep1 or a fragment or variant thereof.

In another preferred embodiment, the invention includes a system for producing pseudouridine wherein said Nep1 comprises a peptide according to SEQ ID NO. 8, or a fragment or variant thereof.

In another preferred embodiment, the invention includes a system for producing pseudouridine wherein said N1-pseudouridine methyltransferase comprises a modified N1-pseudouridine methyltransferase (mNep1).

In another preferred embodiment, the invention includes a system for producing pseudouridine wherein said modified mNep1 comprises a mNep1 wherein 129R and 132R are converted to 129A and 132A.

In another preferred embodiment, the invention includes a system for producing pseudouridine wherein said modified N1-pseudouridine methyltransferase comprises a peptide according to SEQ ID NO. 9, or a fragment or variant thereof.

In another preferred embodiment, the invention includes a system for producing pseudouridine wherein said nuclease is selected from nuclease P1, or 5'-Phosphodiesterase (5'-PDase), or a fragment or variant thereof.

In another preferred embodiment, the invention includes a system for producing pseudouridine further comprising a m1ΨMP purification apparatus.

In another preferred embodiment, the invention includes a system for producing pseudouridine wherein said step of m1ΨMP purification apparatus comprises a weak anion exchange column.

In another preferred embodiment, the invention includes a system for producing pseudouridine wherein said NdK is an adenosyl kinase (AdK) according to: SEQ ID NO. 10, or a fragment or variant thereof.

In another preferred embodiment, the invention includes a system for producing pseudouridine and further comprising an ATP regeneration system comprising:
 a polyphosphate kinase (PPK2);
 adenosyl kinase (AdK);
 inorganic polyphosphate; and
 and adenosine monophosphate (AMP).

In another preferred embodiment, the invention includes a system for producing pseudouridine wherein said PPK2 is selected from the group consisting of: SEQ ID NO's. 4, 6, or a fragment or variant thereof.

In another preferred embodiment, the invention includes a system for producing pseudouridine wherein said AdK comprises a peptide according to SEQ ID NO. 10, or a fragment or variant thereof.

In another preferred embodiment, the invention includes a system for producing pseudouridine further comprising an in vitro transcription system.

In another preferred embodiment, the invention includes a system for producing pseudouridine wherein said in vitro transcription system comprises an in vitro RNA production system.

In one preferred embodiment, the invention includes a method for producing pseudouridine comprising catalyzing the formation of pseudouridine-5'-monophosphate (ΨMP) from a uracil nucleobase with a ribose-5-phosphate with a pseudouridine-5'-phosphate glycosidase (PsuG) enzyme.

In another preferred embodiment, the invention includes a method for producing pseudouridine wherein said PsuG is selected from: SEQ ID NO. 1-2, or a fragment or variant thereof.

In another preferred embodiment, the invention includes a method for producing pseudouridine wherein the concentration of uracil nucleobase and ribose-5-phosphate substrates and reaction temperature cause the reverse catalyzation of the substrates by PsuG forming ΨMP.

In another preferred embodiment, the invention includes a method for producing pseudouridine further comprising the step of generating pseudouridine-5'-triphosphate (ΨTP) from ΨMP by contacting said ΨTP with PPK2 in the present of an inorganic polyphosphate.

In another preferred embodiment, the invention includes a method for producing pseudouridine wherein said inorganic polyphosphate comprises sodium hexamethaphosphate.

In another preferred embodiment, the invention includes a method for producing pseudouridine further comprising the step of methylating said ΨTP forming N1-methyl-pseudouridine-5'-triphosphate (m1ΨTP).

In another preferred embodiment, the invention includes a method for producing pseudouridine wherein said step of methylating comprising contacting said ΨTP with a N1-pseudouridine methyltransferase, or a fragment or variant thereof, forming N1-methyl-pseudouridine (m1Ψ).

In another preferred embodiment, the invention includes a method for producing pseudouridine wherein said N1-pseudouridine methyltransferase comprises a N1-pseudouridine methyltransferase according to SEQ ID NO. 8.

In another preferred embodiment, the invention includes a method for producing pseudouridine wherein said step of generating comprises the step of contacting said ΨMP with a nucleoside diphosphate kinase (NdK) in the presence of an adenosine-triphosphate (ATP) donor.

In another preferred embodiment, the invention includes a method for producing pseudouridine wherein said NdK is an adenosyl kinase (AdK) according to: SEQ ID NO. 10, or a fragment or variant thereof.

In another preferred embodiment, the invention includes a method for producing pseudouridine further comprising the step of isolating said ΨTP.

In another preferred embodiment, the invention includes a method for producing pseudouridine further comprising the step of regenerating said ATP donor by contacting adenosine-monophosphate (AMP) is a Polyphosphate kinase (PPK) or enzyme in the presence of inorganic polyphosphate.

In another preferred embodiment, the invention includes a method for producing pseudouridine wherein said PPK2 is selected from the group consisting of: SEQ ID NO's. 4, 6, or a fragment or variant thereof.

In another preferred embodiment, the invention includes a method for producing pseudouridine wherein one or more of said steps of the invention are performed in an in vitro transcription system.

In another preferred embodiment, the invention includes a method for producing pseudouridine wherein said step of regenerating is performed in an in vitro transcription system.

In another preferred embodiment, the invention includes a method for producing pseudouridine wherein said in vitro transcription system comprises an in vitro RNA production system.

In one preferred embodiment, the invention includes a system for producing pseudouridine comprising:
- a quantity of pseudouridine-5'-phosphate glycosidase (PsuG) enzyme; and
- a substrate comprising:
  - a quantity of uracil nucleobase;
  - a quantity of ribose-5-phosphate;
  - wherein said PsuG catalyzes the formation of pseudouridine-5'-monophosphate (ΨMP) from said substrate.

In another preferred embodiment, the invention includes a system for producing pseudouridine wherein said PsuG is selected from: SEQ ID NO. 1-2, or a fragment or variant thereof.

In another preferred embodiment, the invention includes a system for producing pseudouridine wherein the concentration of uracil nucleobase and ribose-5-phosphate substrates and reaction temperature cause the reverses catalyzation of the substrates by PsuG forming ΨMP.

In another preferred embodiment, the invention includes a system for producing pseudouridine further comprising a quantity of PPK2 and inorganic polyphosphate, wherein said PPK2 and inorganic polyphosphate catalyzed the formation of pseudouridine-5'-triphosphate (ΨTP) from ΨMP.

In another preferred embodiment, the invention includes a system for producing pseudouridine wherein said inorganic polyphosphate comprises sodium hexamethaphosphate.

In another preferred embodiment, the invention includes a system for producing pseudouridine further comprising a quantity of N1-pseudouridine methyltransferase, or a fragment or variant thereof, that methylates said ΨTP forming N1-methyl-pseudouridine-5'-triphosphate (m1ΨTP).

In another preferred embodiment, the invention includes a system for producing pseudouridine wherein said N1-pseudouridine methyltransferase comprises a N1-pseudouridine methyltransferase according to SEQ ID NO. 8.

In another preferred embodiment, the invention includes a system for producing pseudouridine further comprising an ATP regeneration system comprising:
- a polyphosphate kinase (PPK2);
- adenosyl kinase (AdK);
- inorganic polyphosphate; and
- and adenosine monophosphate (AMP).

In another preferred embodiment, the invention includes a system for producing pseudouridine wherein said NdK is an adenosyl kinase according to: SEQ ID NO. 10, or a fragment or variant thereof.

In another preferred embodiment, the invention includes a system for producing pseudouridine wherein said PPK2 is selected from the group consisting of: SEQ ID NO's. 4, 6, or a fragment or variant thereof.

In another preferred embodiment, the invention includes a system for producing pseudouridine further comprising an in vitro transcription system.

In another preferred embodiment, the invention includes a system for producing pseudouridine wherein said step of regenerating is performed in an in vitro transcription system.

In another preferred embodiment, the invention includes a system for producing pseudouridine wherein said in vitro transcription system comprises an in vitro RNA production system.

In another preferred embodiment, the invention includes an isolated nucleotide sequence encoding a peptide selected from the group consisting of: SEQ ID NO's. 1-21, or a combination, fragment, or variant of the same.

In another preferred embodiment, the invention includes an isolated expression vector having a nucleotide sequence, operably linked to a promoter, encoding a peptide selected from the group consisting of: to SEQ ID NO's. 1-21, or a combination, fragment or variant of the same.

SEQUENCE LISTING

```
Sequence total quantity: 22
SEQ ID NO: 1           moltype = AA  length = 312
FEATURE                Location/Qualifiers
source                 1..312
                       mol_type = protein
                       organism = Escherichia coli
SEQUENCE: 1
MSKLKISPEL LQISPEVQEA LKNKKPVVAL ESTIISHGMP FPQNAQTAIE VEETIRKQGA  60
VPATIAIIGG VMKVGLSKEE IELLGREGHN VTKVSRRDLP FVVAAGKNGA TTVASTMIIA  120
ALAGIKVFAT GGIGGVHRGA EHTFDISADL QELANTNVTV VCAGAKSILD LGLTTEYLET  180
FGVPLIGYQT KALPAFFCRT SSFDVSIRLD SASEIARAMA VKWQSGLNGG LVVANPIPEQ  240
FAMPEESINA AIDQAVAEAE EQGVIGKEST PFLLARVAEL TGGDSLKSNI QLVFNNAILA  300
SEIAKEYQRL AG                                                    312

SEQ ID NO: 2           moltype = AA  length = 327
FEATURE                Location/Qualifiers
source                 1..327
                       mol_type = protein
                       organism = Escherichia coli
SEQUENCE: 2
MGSSHHHHHH SSGGSMSKLK ISPELLQISP EVQEALKNKK PVVALESTII SHGMPFPQNA  60
QTAIEVEETI RKQGAVPATI AIIGGVMKVG LSKEEIELLG REGHNVTKVS RRDLPFVVAA  120
GKNGATTVAS TMIIAALAGI KVFATGGIGG VHRGAEHTFD ISADLQELAN TNVTVVCAGA  180
KSILDLGLTT EYLETFGVPL IGYQTKALPA FFCRTSSFDV SIRLDSASEI ARAMAVKWQS  240
GLNGGLVVAN PIPEQFAMPE ESINAAIDQA VAEAEEQGVI GKESTPFLLA RVAELTGGDS  300
LKSNIQLVFN NAILASEIAK EYQRLAG                                    327

SEQ ID NO: 3           moltype = AA  length = 313
FEATURE                Location/Qualifiers
source                 1..313
                       mol_type = protein
                       organism = Deinococcus geothermalis
SEQUENCE: 3
```

```
MLTPIPSQVT QLMDLHPEVA AALTAGHPVV ALESTIISHG MPYPQNVEMA TGVETIVREN    60
GATPATIAVL GGRLKVGLTP DELEQLATDR RVQKISTRDL PFTVALGGHG ATTVAATMRI   120
AALAGIRVFA TGGTGGVHRG ASESMDISAD LTELARTDVC VVSAGVKSIL DIGLTLEVLE   180
THGVPTLTLG SEEFPAFYSR RSGFASPLTV QTEAEAARVL HAKWTLGLTG GVLLANPIPE   240
DAEIPAAEIS PHIEQALADM AALGLTGKAT TPYLLGRLVE ITGGRSLAAN IALVRHNAAV   300
AARVASAYAA LQG                                                     313

SEQ ID NO: 4           moltype = AA  length = 266
FEATURE                Location/Qualifiers
source                 1..266
                       mol_type = protein
                       organism = Deinococcus geothermalis
SEQUENCE: 4
MQLDRYRVPP GQRVRLSNWP TDDDGGLSKA EGEALLPDLQ QRLANLQERL YAESQQALLI    60
VLQARDAGGK DGTVKHVIGA FNPSGVQVSN FKVPTEEERA HDFLWRIHRQ TPRLGMIGVF   120
NRSQYEDVLV TRVHHLIDDQ TAQRRLKHIC AFESLLTDSG TRIVKFYLHI SPEEQKKRLE   180
ARLADPSKHW KFNPGDLQER AHWDAYTAVY EDVLTTSTPA APWYVVPADR KWFRNLLVSQ   240
ILVQTLEEMN PQFPAPAFNA ADLRIV                                       266

SEQ ID NO: 5           moltype = AA  length = 301
FEATURE                Location/Qualifiers
source                 1..301
                       mol_type = protein
                       organism = Deinococcus geothermalis
SEQUENCE: 5
MGSSHHHHHH SSGENLYFQG HMASMTGGQQ MGRGSMQLDR YRVPPGQRVR LSNWPTDDDG    60
GLSKAEGEAL LPDLQQRLAN LQERLYAESQ QALLIVLQAR DAGGKDGTVK HVIGAFNPSG   120
VQVSNFKVPT EEERAHDFLW RIHRQTPRLG MIGVFNRSQY EDVLVTRVHH LIDDQTAQRR   180
LKHICAFESL LTDSGTRIVK FYLHISPEEQ KKRLEARLAD PSKHWKFNPG DLQERAHWDA   240
YTAVYEDVLT TSTPAAPWYV VPADRKWFRN LLVSQILVQT LEEMNPQFPA PAFNAADLRI   300
V                                                                  301

SEQ ID NO: 6           moltype = AA  length = 267
FEATURE                Location/Qualifiers
source                 1..267
                       mol_type = protein
                       organism = Meiothermus ruber
SEQUENCE: 6
MKKYRVQPDG RFELKRFDPD DTSAFEGGKQ AALEALAVLN RRLEKLQELL YAEGQHKVLV    60
VLQAMDAGGK DGTIRVVFDG VNPSGVRVAS FGVPTEQELA RDYLWRVHQQ VPRKGELVIF   120
NRSHYEDVLV VRVKNLVPQQ VWQKRYRHIR EFERMLADEG TTILKFFLHI SKDEQRQRLQ   180
ERLDNPEKRW KFRMGDLEDR RLWDRYQEAY EAAIRETSTE YAPWYVIPAN KNWYRNWLVS   240
HILVETLEGL AMQYPQPETA SEKIVIE                                      267

SEQ ID NO: 7           moltype = AA  length = 302
FEATURE                Location/Qualifiers
source                 1..302
                       mol_type = protein
                       organism = Meiothermus ruber
SEQUENCE: 7
MGSSHHHHHH SSGENLYFQG HMASMTGGQQ MGRGSMKKYR VQPDGRFELK RFDPDDTSAF    60
EGGKQAALEA LAVLNRRLEK LQELLYAEGQ HKVLVVLQAM DAGGKDGTIR VVFDGVNPSG   120
VRVASFGVPT EQELARDYLW RVHQQVPRKG ELVIFNRSHY EDVLVRVKN LVPQQVWQKR   180
YRHIREFERM LADEGTTILK FFLHISKDEQ RQRLQERLDN PEKRWKFRMG DLEDRRLWDR   240
YQEAYEAAIR ETSTEYAPWY VIPANKNWYR NWLVSHILVE TLEGLAMQYP QPETASEKIV   300
IE                                                                 302

SEQ ID NO: 8           moltype = AA  length = 252
FEATURE                Location/Qualifiers
source                 1..252
                       mol_type = protein
                       organism = Saccharomyces cerevisiae
SEQUENCE: 8
MVEDSRVRDA LKGGDQKALP ASLVPQAPPV LTSKDKITKR MIVVLAMASL ETHKISSNGP    60
GGDKYVLLNC DDHQGLLKKM GRDISEARPD ITHQCLLTLL DSPINKAGKL QVYIQTSRGI   120
LIEVNPTVRI PRTFKRFSGL MVQLLHKLSI RSVNSEEKLL KVIKNPITDH LPTKCRKVTL   180
SFDAPVIRVQ DYIEKLDDDE SICVFVGAMA RGKDNFADEY VDEKVGLSNY PLSASVACSK   240
FCHGAEDAWN IL                                                      252

SEQ ID NO: 9           moltype = AA  length = 252
FEATURE                Location/Qualifiers
source                 1..252
                       mol_type = protein
                       organism = Saccharomyces cerevisiae
SEQUENCE: 9
MVEDSRVRDA LKGGDQKALP ASLVPQAPPV LTSKDKITKR MIVVLAMASL ETHKISSNGP    60
GGDKYVLLNC DDHQGLLKKM GRDISEARPD ITHQCLLTLL DSPINKAGKL QVYIQTSRGI   120
LIEVNPTVAI PATFKRFSGL MVQLLHKLSI RSVNSEEKLL KVIKNPITDH LPTKCRKVTL   180
SFDAPVIRVQ DYIEKLDDDE SICVFVGAMA RGKDNFADEY VDEKVGLSNY PLSASVACSK   240
```

```
FCHGAEDAWN IL                                                              252

SEQ ID NO: 10            moltype = AA  length = 224
FEATURE                  Location/Qualifiers
source                   1..224
                         mol_type = protein
                         organism = Geobacillus stearothermophilus
SEQUENCE: 10
SGSSMNLVLM GLPGAGKGTQ AGKIVEAYGI FHISTGDMFR AAIKEGTPLG LQAKQYMDRG   60
DLVPDELQAK QYMDRGDLVP DEGFLLDGFP RTVAQAEALE TLLSSIGRKL DYVIHIDVRQ  120
EVLMERLTGR RICRNCGATY HLVFHPPAKP GVCDKCGGDL YQRPDNEATV ANRLEVNMKQ  180
MKLLLDFYEQ KGYLRHINGE QEMEKVFADI CEVLGGLARG RRAA                  224

SEQ ID NO: 11            moltype = AA  length = 543
FEATURE                  Location/Qualifiers
source                   1..543
                         mol_type = protein
                         organism = Saccharomyces cerevisiae
SEQUENCE: 11
SEENLRPAYD DQVNEDVYKR GAQSKLTKAR KADFDDEKDK KDNDKHIDK  RPKSGPRLDE   60
NGNPLPKEPR LPKRKVAVMV GYCGTGYHGM QYNPPNPTIE SALFKAFVEA GAISKDNSND  120
LKKNGFMRAA RTDKGVHAGG NLISLKMIIE DPDIKQKINE KLPEGIRVWD IERVNKAFDC  180
RKMCSSRWYE YLLPTYSLIG PKPGSILYRD IEESKTELPG VLDEDLESKE FWEEFKKDAN  240
EKFSTEEIEA ILAYVPPARD EFDINEELYQ KVKKYKQLEN AHRRRYRISA AKLAKFRAST  300
SQYLGAHNFH NFTLGKDFKE PSAIRFMKDI KVSDPFVIGD AQTEWISIKI HGQSFMLHQI  360
RKMVSMATLI TRCGCPVERI SQAYGQQKIN IPKAPALGLL LEAPVFEGYN KRLEQFGYKA  420
IDFSKYQDEV DKFKMKHIYD KIYKEEVDEN VFNAFFSYID SFNKVTGAQG EETADKSGPA  480
VQKSIFEFLT AKGIPGLTDA PESNKKIKQR KRMEEEEAAS KKAEISSTTQ SNEPEVQPEA  540
AAN                                                                543

SEQ ID NO: 12            moltype = AA  length = 369
FEATURE                  Location/Qualifiers
source                   1..369
                         mol_type = protein
                         organism = Saccharomyces cerevisiae
SEQUENCE: 12
LLGYCGSGYY GMQYNPPHKT IEGEILTKLF DVGAISEENS LAPKKNSFMA AARTDKGVHA   60
MLNLLSLKIT LREDTVAKLN AALPPEIRVW GIQPVNKKFN ARSACDSRWY QYLIPEFILI  120
GPPRSSLLHR NVGGCYREDG SQEVWDTFLE QTRGRFSGDE LCRLQDTAQK LSESDPLVQD  180
YVGLLSGTLS GYCLSPSKLD AFEAAMQEYV GTHNFHNFTT GKLWGDPSAQ RHIKKVVVSQ  240
ASPGWICVRI HGQSFMLHQI RRMVALAVLA ARCQLPPNIV RNYFNAGPRK YIPRAPAQGL  300
LLEGPVFDGY NTKLRNLLYC EIRPDDITLE RMCRFREROI CTAIAHEETO RHVFCHFVRQ  360
MNRLATPLI                                                          369

SEQ ID NO: 13            moltype = AA  length = 441
FEATURE                  Location/Qualifiers
source                   1..441
                         mol_type = protein
                         organism = Saccharomyces cerevisiae
SEQUENCE: 13
SNFIRRLVGK MKAISTGTNA IVSKKDSIYA NWSKEQLIRR ITELENANKP HSEKFQHIED   60
NKKRKISQEE VTRSKAKKAP KKFDFSKHNT RFIALRFAYL GWNYNGLAVQ KEYTPLPTVE  120
GTILEAMNKC KLVPSMVLQD YKFSRCGRTD KGVSAMNQVI SLEVRSNLTD EEQRDPTNDS  180
REIPYVHVLN QLLPDDIRIS AVCLRPPPNF DARFSCVHRH YKYIFNGKNL NIEKMSKAAS  240
YFVGERDFRN FCKLDGSKQI TNFKRTIISS KILPLSETFY CFDLVGSAFL WHQVRCMMAI  300
LFLVGQSLEV PEIVLRLTDI EKTPQRPVYE MANDIPLLLY DCKFPEMDWQ EPTVDDYKAI  360
KFTTATEALT LHYELKAAVC NIFKDVLPTA NTNNFSKTII NLGDGRGKVV GTYVKLEDRS  420
VMEPVEVVNA KYSKKKNNKN K                                            441

SEQ ID NO: 14            moltype = AA  length = 402
FEATURE                  Location/Qualifiers
source                   1..402
                         mol_type = protein
                         organism = Saccharomyces cerevisiae
SEQUENCE: 14
NGIFAIEKPS GITSNQFMLK LQHALTKSQV FSKEIQRATA ERKQQYEKQT GKKASKRKLR   60
KVSKVKMGHG GTLDPLASGV LVIGIGAGTK KLANYLSGTV KVYESEALFG VSTTSGDVEG  120
EILSQNSVKH LNFDDLKTVE EKFVGQLKQT PPIYAALKMD GKPLHEYARE GKPLPRAIEP  180
RQVTIYDLKV FSDSLKRDHD YPLLRPTTEE AVDTVKNLNA NMLNDVLYFS KEYTEKHGLD  240
SEVAKVEEPF PLSEQEEQEI QKEGDSYRAP KLHFKANVSS GTYIRSLVSD IGKSMRSSCY  300
MVKLIRLQQQ DWSLEKNNVF QLTDFTERDE KVWSKVLEKV LDEGATVDVI EELKKAEKEI  360
PADVKECIVS SDQPGDEATA ETIETANAEE HSNTLKRKIE QV                     402

SEQ ID NO: 15            moltype = AA  length = 253
FEATURE                  Location/Qualifiers
source                   1..253
                         mol_type = protein
                         organism = Saccharomyces cerevisiae
SEQUENCE: 15
```

```
SLKKQIPIIF ENTHYFIVNK PPGIPSQPPD CRTWGRTHPN LDPTPLLERF KAIYYSHREV    60
ELCRTVHRLD HCVTGGMLIA KTKDGSVKFS RFLQKGGNNG YKLQRKYVAI VESSGRFNKP   120
NNYEIKYGPK YNFLISHGGR EITKFKEVDE NCIVLQLVTG KKHQIRNHVS QILNQPILND   180
KRHGSTVNFP ELFNDQIALH SACIITKIGL QTKTHLIPME HNNTGQLWSR KYVNEEGEFT   240
LPIKEVLLEN WDQ                                                      253

SEQ ID NO: 16           moltype = AA  length = 403
FEATURE                 Location/Qualifiers
source                  1..403
                        mol_type = protein
                        organism = Saccharomyces cerevisiae
SEQUENCE: 16
STIKVIEVYT QNGLRKVRPY YNRRSAFVKG RWLGKLLIDV LVSEFKLRPR AYYLDQIRKG    60
TYRLIRDGVP LVPDHLMTTI IKNHDVLETT THKHEPPVKQ WCSQEVEAED LPGRIAGFNI   120
VFEDESILVI DKPSGIPVHP TGQFYQNTIT ELLKLHGVDA LPCYRLDKIT SGLLILAKNS   180
QSAGEIQKSI RSRDMIKIYL ARVKGRFPHS ELILDNENAA ETTFEDTSKV TVEMTPIYSI   240
DPKRQFPVGL STSKDAITKF YPIRYFSHAD ETVVACKPIT GRTHQIRIHL ARLGHPIVND   300
SVYCSHITKY PERLKFITQF PRWENQQDLD AEELKVRFQK FVDETKNNCR TMETFCPECH   360
TVDLKDPVLS DLELWLHAWK YEEINGKFKF KTDLPKWAQL DNS                     403

SEQ ID NO: 17           moltype = AA  length = 675
FEATURE                 Location/Qualifiers
source                  1..675
                        mol_type = protein
                        organism = Saccharomyces cerevisiae
SEQUENCE: 17
SDSSEATVKR PLDAHVGPSE NAAKKLKIEQ RTQADGIHEA DVGITLFLSP ELPGFRGQIK    60
QRYTDFLVNE IDQEGKVIHL TDKGFKMPKK PQRSKEEVNA EKESEAARRQ EFNVDPELRN   120
QLVEIFGEED VLKIESVYRT ANKMETAKNF EDKSVRTKIH QLLREAFKNE LESVTTDTNT   180
FKIARSNRNS RTNKQEKINQ TRDANGVENW GYGPSKDFIN FTLHKENKDT MEAVNVITKL   240
LRVPSRVIRY AGTKDRRAVT CQRVSISKIG LDRLNALNRT LKGMIIGNYN FSDASLNLGD   300
LKGNEFVVVI RDVTTGNSEV SLEEIVSNGC KSLSENGFIN YFGMQRFGTF SISTHTIGRE   360
LLLSNWKKAA ELILSDQDNV LPKSKEARKI WAETKDAALA LKQMPRQCLA ENALLYSLSN   420
QRKEEDGTYS ENAYYTAIMK IPRNLRTMYV HAYQSYVWNS IASKRIELHG LKLVVGDLVI   480
DTSEKSPLIS GIDDEDFDED VREAQFIRAK AVTQEDIDSV KYTMEDVVLP SPGFDVLYPS   540
NEELKQLYVD ILKADNMDPF NMRRKVRDFS LAGSYRTVIQ KPKSLEYRII HYDDPSQQLV   600
NTDLDILNNT RAKESGQKYM KAKLDRYMPD KGGEKTAVVL KFQLGTSAYA TMALRELMKL   660
ETSRRGDMCD VKENI                                                    675

SEQ ID NO: 18           moltype = AA  length = 431
FEATURE                 Location/Qualifiers
source                  1..431
                        mol_type = protein
                        organism = Saccharomyces cerevisiae
SEQUENCE: 18
EDSNNEASDD FNNLLNKEIE SAKEVKLRKF ANRNNNRNEN SSKVKDASGF RLRVIQTDGH    60
KTKKTDPDYE VTIDGPLRKI EPYFFTYKTF CKERWRDRKL VDVFVSEFRD REPSYYSKTI   120
AEGKVYLNDE PANLDTIIRD GDLITHKVHR HEPPVTSKPI DIVFEDEDIL VIDKPSSIPV   180
HPTGRYRFNT ITKMLERQLG YSVHPCNRLD KPTSGLMFLA KTPLGADRMG DQMKAREVTK   240
EYVARVKGEF PIGIVEVDKP VRSVNPKVAL NAVCEMSDEN AKHAKTVFQR VSYDGQTSIV   300
KCKPLTGRTH QIRVHLQYLG FPIANDPIYS NPDIWGPDLG RGGLQNYDDI VLKLDAIGKT   360
NPAESWIHPH SEGEYLLGRQ CEECEAEMYT DPGTNDLDLW LHAFRYESLE RNSDTQKPLW   420
SYRTKYPEWA L                                                        431

SEQ ID NO: 19           moltype = AA  length = 438
FEATURE                 Location/Qualifiers
source                  1..438
                        mol_type = protein
                        organism = Saccharomyces cerevisiae
SEQUENCE: 19
ALSAGLAFAG NATSNEFDEH LQNEVERERE IQKKKKIKRT QSKKSPDLIN KSTFQSRTIG    60
SKKEKHRQLD PEYEIVIDGP LRKIKPYHFT YRTFCKERWR DKKLVDVFIS EFRDRESEYY   120
KRTIENGDVH INDETADLST VIRNGDLITH QVHRHEPPVT SRPIKVIFED DNIMVIDKPS   180
GIPVHPTGRY RFNTITKMLQ NNLGFVVNPC NRLDRLTSGL MFLAKTPKGA DNIGDQLKAR   240
EVTKEYVAKV VGEFPETEVI VEKPLKLIEP RLALNAVCQM DEKGAKHAKT VFNRISYDGK   300
TSIVKCKPLT GRSHQIRVHL QYLGHPIAND PIYSNDEVWG NNLGKGGQAD FDIVITKLDE   360
IGKRKPAKSW FHSNGGYGEV LRQEKCSICE SDLYTDPGPN DLDLWLHAYL YESTETEEGT   420
EKKKWCYKTE YPEWALRR                                                 438

SEQ ID NO: 20           moltype = AA  length = 295
FEATURE                 Location/Qualifiers
source                  1..295
                        mol_type = protein
                        organism = Deinococcus geothermalis
SEQUENCE: 20
MRVLVVGSVN ADITVRAPRI PAPGETVLGE DARVSPGGKG ANQAVAAALA GASVALCGAV    60
GRDAFREAAL SGLTRAGVDL TWLHELDAPT GLALITVAAG GENAITVASG ANARVTPAQL   120
PADLTGFTHL LLQGELPVAV TREAARRAHA AGLTVLHNAA PARNPDPDLL AYTHHLIVNE   180
HELAALAGGG EAIDAQARAL LPRGPQAVTV TLGARGSLTV TAETTYRLPA FPVTSVDTTG   240
```

```
AGDTFCGVLT AWLAQGHALQ GALHAAGVAA ALACTRPGAQ DAMPSRAELA AALAR              295

SEQ ID NO: 21           moltype = AA  length = 266
FEATURE                 Location/Qualifiers
source                  1..266
                        mol_type = protein
                        organism = Deinococcus radiodurans
SEQUENCE: 21
MDIDNYRVKP GKRVKLSDWA TNDDAGLSKE EGQAQTAKLA GELAEWQERL YAEGKQSLLL        60
ILQARDAAGK DGAVKKVIGA FNPAGVQITS FKQPSAEELS HDFLWRIHQK APAKGYVGVF        120
NRSQYEDVLV TRVYDMIDDK TAKRRLEHIR HFEELLTDNA TRIVKVYLHI SPEEQKERLQ        180
ARLDNPGKHW KFNPGDLKDR SNWDKFNDVY EDALTTSTDD APWYVVPADR KWYRDLVLSH        240
ILLGALKDMN PQFPAIDYDP SKVVIH                                            266

SEQ ID NO: 22           moltype = AA  length = 301
FEATURE                 Location/Qualifiers
source                  1..301
                        mol_type = protein
                        organism = Deinococcus radiodurans
SEQUENCE: 22
MGSSHHHHHH SSGENLYFQG HMASMTGGQQ MGRGSMDIDN YRVKPGKRVK LSDWATNDDA        60
GLSKEEGQAQ TAKLAGELAE WQERLYAEGK QSLLLILQAR DAAGKDGAVK KVIGAFNPAG        120
VQITSFKQPS AEEELSHDFLW RIHQKAPAKG YVGVFNRSQY EDVLVTRVYD MIDDKTAKRR       180
LEHIRHFEEL LTDNATRIVK VYLHISPEEQ KERLQARLDN PGKHWKFNPG DLKDRSNWDK        240
FNDVYEDALT TSTDDAPWYV VPADRKWYRD LVLSHILLGA LKDMNPQFPA IDYDPSKVVI        300
H                                                                       301
```

What is claimed is:

1. A system for the production of pseudouridine compounds comprising:
   an isolated uracil nucleobase, and isolated ribose-5-phosphate, wherein the uracil nucleobase with the ribose-5-phosphate are converted to form pseudouridine-5'-monophosphate (ΨMP), wherein the formation of ΨMP is catalyzed by pseudouridine-5'-phosphate glycosidase, or a functional fragment or variant thereof;
   a protecting agent that reacts with the hydroxyl groups of said ΨMP forming a protected ΨMP;
   a methylating agent that reacts with the protected ΨMP, forming a protected N1-methyl -pseudouridine-5'-monophosphate (protected m1ΨMP) compound;
   a deprotection agent that reacts with the protected m1ΨMP forming N1-methyl-pseudouridine-5'-monophosphate (m1ΨMP); and
   a phosphorylating agent that catalyzes the sequential phosphorylation of m1MP forming N1-methyl-pseudouridine-5'-diphosphate (m1ΨTP), and N1-methyl-pseudouridine-5'-triphosphate (m1ΨTP).

2. The system of claim 1, wherein said protecting agent comprises a N-silyl compound.

3. The system of claim 2, wherein said N-silyl compound comprises hexamethyldisilazane (HMDS), wherein said HMDS reacts with the ΨMP forming a protected ΨMP.

4. The system of claim 1, wherein said methylating agent comprises iodomethane.

5. The system of claim 1, wherein said deprotection agent comprises ammonia and methanol.

6. The system of claim 1, wherein said phosphorylating agent comprises polyphosphate kinase (PPK2), or a functional fragment thereof, and inorganic polyphosphate, wherein said PPK2, or the functional fragment thereof, catalyzes the sequential phosphorylation of m1ΨMP to form m1ΨDP and m1ΨTP.

7. The system of claim 6, wherein a concentration of inorganic polyphosphate is in excess, such that it promotes the forward reaction of the sequential phosphorylation of m1ΨMP to form m1ΨDP and m1ΨTP.

8. The system of claim 6, wherein the sequential phosphorylation of m1ΨMP by PPK is performed at a temperature, and in the presence of excess inorganic polyphosphate that generates reaction conditions that causes the forward reaction of the sequential phosphorylation of m1ΨMP to form m1ΨDP and m1ΨTP.

9. The system of claim 6, wherein said PPK comprises a PPK from a thermophilic bacterium.

10. The system of claim 9, wherein said thermophilic bacterium is selected from: *Deinococcus geothermalis*, *Deinococcus radiodurans*, or *Meiothermus* Tuber.

11. The system of claim 6, wherein said PPK comprises a sequence selected from the polypeptide sequence of SEQ ID NO. 4, 6, and 21, or a sequence having at least 90% homology with SEQ ID NO. 4, 6, or 21 that catalyzes the sequential phosphorylation of m1ΨMP to form m1ΨDP and m1ΨTP in the presence of inorganic polyphosphate.

12. The system of claim 1, wherein said pseudouridine-5'-phosphate glycosidase is from a thermophilic bacterium or an enteric bacterium.

13. The system of claim 1, wherein said pseudouridine-5'-phosphate glycosidase comprises a sequence selected from the polypeptide sequence of SEQ ID NO. 1, and 3, or a sequence having at least 90% homology with SEQ ID NO. 1, or 3 that catalyzes the formation of pseudouridine-5'-monophosphate (ΨMP) from uracil nucleobase and ribose-5-phosphate.

14. The system of claim 1, further comprising:
   an isolated Ribokinase (RbsK) enzyme, or a functional fragment thereof, and ribose; and
   wherein said RbsK, or the functional fragment thereof, catalyzes the formation of said ribose-5-phosphate from said ribose in the presence of an adenosine-triphosphate (ATP) donor, which donates a phosphate group to said ribose to form the ribose-5-phosphate and an adenosine-diphosphate (ADP).

15. The system of claim 14, wherein the ATP is enzymatically regenerated from the ADP in the presence of inorganic polyphosphate.

16. The system of claim 14, wherein said RbsK comprises an RbsK from a thermophilic bacterium.

17. The system of claim 16, wherein said thermophilic bacterium comprises Deinococcus geothermalis.

18. The system of claim 14, wherein said RbsK comprises a sequence according to SEQ ID NO. 20, or a sequence having at least 90% homology with SEQ ID NO. 20 that catalyzes the formation of ribose-5-phosphate from ribose in the presence of an adenosine-triphosphate (ATP) donor.

19. The system of claim 1, wherein the concentration of said uracil nucleobase and ribose-5-phosphate and reaction temperature cause the reverse catalyzation of the uracil nucleobase with the ribose-5-phosphate substrates forming the ΨMP.

20. A system for the production of pseudouridine compounds comprising
  an isolated uracil nucleobase, and isolated ribose-5-phosphate, wherein said uracil nucleobase with a ribose-5-phosphate are converted to form pseudouridine-5'-monophosphate (ΨMP), wherein the enzymatic formation of ΨMP is catalyzed by pseudouridine-5'-phosphate glycosidase, or a functional fragment or variant thereof; and
  a protecting agent that reacts with the hydroxyl groups of said ΨMP forming a protected ΨMP.

21. A system for the production of pseudouridine compounds comprising
  an isolated uracil nucleobase, and isolated ribose-5-phosphate, wherein said uracil nucleobase with a ribose-5-phosphate are converted to form pseudouridine-5'-monophosphate (ΨMP), wherein the formation of ΨMP is catalyzed by pseudouridine-5'-phosphate glycosidase or a functional fragment or variant thereof;
  a protecting agent that reacts with the hydroxyl groups of said ΨMP forming a protected ΨMP; and
  a methylating agent that reacts with the protected ΨMP, forming a protected N1-methyl-pseudouridine-5'-monophosphate (protected m1ΨMP) compound.

22. A system for the production of pseudouridine compounds comprising
  an isolated uracil nucleobase, and isolated ribose-5-phosphate, wherein said uracil nucleobase with a ribose-5-phosphate are converted to form pseudouridine-5'-monophosphate (ΨMP), wherein the formation of ΨMP is catalyzed by pseudouridine-5'-phosphate glycosidase or a functional fragment or variant thereof;
  a protecting agent that reacts with the hydroxyl groups of said ΨMP forming a protected ΨMP;
  a methylating agent that reacts with the protected ΨMP, forming a protected N1-methyl-pseudouridine-5'-monophosphate (protected m1MP) compound; and
  a deprotection agent that reacts with the protected m1ΨMP forming N1-methyl-pseudouridine-5'-monophosphate (m1MP).

* * * * *